(12) United States Patent
Addison et al.

(10) Patent No.: US 8,628,477 B2
(45) Date of Patent: Jan. 14, 2014

(54) SYSTEMS AND METHODS FOR NON-INVASIVE DETERMINATION OF BLOOD PRESSURE

(75) Inventors: Paul Stanley Addison, Edinburgh (GB); James Watson, Dunfermline (GB)

(73) Assignee: Nellcor Puritan Bennett Ireland, Galway (IE)

( * ) Notice: Subject to any disclaimer, the term of this patent is extended or adjusted under 35 U.S.C. 154(b) by 735 days.

(21) Appl. No.: 12/533,224

(22) Filed: Jul. 31, 2009

(65) Prior Publication Data

US 2011/0028854 A1 Feb. 3, 2011

(51) Int. Cl.
*A61B 5/02* (2006.01)

(52) U.S. Cl.
USPC .......................................... 600/493; 600/490

(58) Field of Classification Search
USPC ................................................. 600/490–499
See application file for complete search history.

(56) References Cited

U.S. PATENT DOCUMENTS

| | | |
|---|---|---|
| 3,835,840 A | 9/1974 | Mount |
| 4,289,141 A | 9/1981 | Cormier |
| 4,561,447 A | 12/1985 | Kawamura et al. |
| 4,676,253 A | 6/1987 | Newman et al. |
| 4,729,382 A | 3/1988 | Schaffer et al. |
| 4,830,017 A | 5/1989 | Perry et al. |
| 4,836,213 A | 6/1989 | Wenzel et al. |
| 4,854,327 A | 8/1989 | Kunig |
| 4,898,176 A | 2/1990 | Petre |
| 4,924,871 A | 5/1990 | Honeyager |
| 4,928,700 A | 5/1990 | Harada |
| 4,951,679 A | 8/1990 | Harada |
| 4,976,268 A | 12/1990 | Kurosawa et al. |
| 4,987,900 A | 1/1991 | Eckerle et al. |
| 5,065,765 A | 11/1991 | Eckerle et al. |
| 5,103,831 A | 4/1992 | Niwa |
| 5,105,815 A | 4/1992 | Hall et al. |
| 5,119,824 A | 6/1992 | Niwa |
| 5,131,400 A | 7/1992 | Harada et al. |
| 5,163,328 A | 11/1992 | Holland et al. |
| 5,170,796 A | 12/1992 | Kobayashi |
| 5,176,143 A | 1/1993 | Eckerle et al. |
| 5,178,154 A | 1/1993 | Ackmann et al. |
| 5,179,956 A | 1/1993 | Harada et al. |
| 5,204,922 A | 4/1993 | Weir et al. |

(Continued)

FOREIGN PATENT DOCUMENTS

| | | |
|---|---|---|
| DE | 102005007963 A1 | 8/2006 |
| EP | 0443267 | 8/1991 |

(Continued)

OTHER PUBLICATIONS

Addison, Paul S., The Illustrated Wavelet Transform Handbook, Taylor & Francis Group, 2002.

(Continued)

*Primary Examiner* — Patricia Mallari
*Assistant Examiner* — Tiffany Weston

(57) ABSTRACT

Methods and systems for determining blood pressure from a pressure signal are disclosed. A patient's blood pressure may be determined by analyzing features of a wavelet transformation of a pressure signal obtained during an occlusion procedure. Ridges in a scalogram of the transformed signal may be identified and used to determine an envelope of a pressure oscillation signal, to which oscillometric blood pressure determination techniques may be applied.

20 Claims, 14 Drawing Sheets

(56) References Cited

U.S. PATENT DOCUMENTS

| | | |
|---|---|---|
| 5,238,000 A | 8/1993 | Niwa |
| 5,241,964 A | 9/1993 | McQuilkin |
| 5,255,686 A | 10/1993 | Takeda et al. |
| 5,269,312 A | 12/1993 | Kawamura et al. |
| 5,289,823 A | 3/1994 | Eckerle |
| 5,309,917 A | 5/1994 | Wang et al. |
| 5,431,159 A | 7/1995 | Baker et al. |
| 5,439,483 A | 8/1995 | Duong-Van |
| 5,450,852 A | 9/1995 | Archibald et al. |
| 5,467,771 A | 11/1995 | Narimatsu et al. |
| 5,490,506 A | 2/1996 | Takatani et al. |
| 5,494,043 A | 2/1996 | O'Sullivan et al. |
| 5,497,779 A | 3/1996 | Takaya et al. |
| 5,505,209 A | 4/1996 | Reining |
| 5,533,511 A | 7/1996 | Kaspari et al. |
| 5,535,753 A | 7/1996 | Petrucelli et al. |
| 5,562,621 A | 10/1996 | Claude et al. |
| 5,564,427 A | 10/1996 | Aso et al. |
| 5,575,284 A | 11/1996 | Athan et al. |
| 5,590,650 A | 1/1997 | Genova |
| 5,617,868 A | 4/1997 | Harada et al. |
| 5,632,272 A | 5/1997 | Diab et al. |
| 5,640,964 A | 6/1997 | Archibald et al. |
| 5,649,542 A | 7/1997 | Archibald et al. |
| 5,649,543 A | 7/1997 | Hosaka et al. |
| 5,676,140 A | 10/1997 | Ukawa et al. |
| 5,682,898 A | 11/1997 | Aung et al. |
| 5,685,316 A | 11/1997 | Schookin et al. |
| 5,704,362 A | 1/1998 | Hersh et al. |
| 5,709,212 A | 1/1998 | Sugo et al. |
| 5,720,292 A | 2/1998 | Poliac |
| 5,722,414 A | 3/1998 | Archibald et al. |
| 5,738,103 A | 4/1998 | Poliac |
| 5,743,856 A | 4/1998 | Oka et al. |
| 5,755,669 A | 5/1998 | Ono et al. |
| 5,762,610 A | 6/1998 | Narimatsu et al. |
| 5,772,601 A | 6/1998 | Oka et al. |
| 5,772,602 A | 6/1998 | Sakai et al. |
| 5,776,071 A | 7/1998 | Inukai et al. |
| 5,778,881 A | 7/1998 | Sun et al. |
| 5,785,659 A | 7/1998 | Caro et al. |
| 5,791,347 A | 8/1998 | Flaherty et al. |
| 5,795,304 A | 8/1998 | Sun et al. |
| 5,797,395 A | 8/1998 | Martin |
| 5,797,840 A | 8/1998 | Akselrod et al. |
| 5,797,850 A | 8/1998 | Archibald et al. |
| 5,810,736 A | 9/1998 | Pail |
| 5,827,181 A | 10/1998 | Dias et al. |
| 5,827,195 A | 10/1998 | Lander |
| 5,830,131 A | 11/1998 | Caro et al. |
| 5,832,924 A | 11/1998 | Archibald et al. |
| 5,833,618 A | 11/1998 | Caro et al. |
| 5,848,970 A | 12/1998 | Voss et al. |
| 5,857,975 A | 1/1999 | Golub |
| 5,873,834 A | 2/1999 | Yanagi et al. |
| 5,904,654 A | 5/1999 | Wohltmann et al. |
| 5,919,134 A | 7/1999 | Diab |
| 5,941,828 A | 8/1999 | Archibald et al. |
| 5,964,711 A | 10/1999 | Voss et al. |
| 5,967,995 A | 10/1999 | Shusterman et al. |
| 6,002,952 A | 12/1999 | Diab et al. |
| 6,004,274 A | 12/1999 | Nolan et al. |
| 6,007,492 A | 12/1999 | Goto et al. |
| 6,011,986 A | 1/2000 | Diab et al. |
| 6,022,320 A | 2/2000 | Ogura et al. |
| 6,027,452 A | 2/2000 | Flaherty et al. |
| 6,027,453 A | 2/2000 | Miwa et al. |
| 6,027,455 A | 2/2000 | Inukai et al. |
| 6,036,653 A | 3/2000 | Baba et al. |
| 6,045,509 A | 4/2000 | Caro et al. |
| 6,067,462 A | 5/2000 | Diab et al. |
| 6,083,171 A | 7/2000 | Ono et al. |
| 6,094,592 A | 7/2000 | Yorkey et al. |
| 6,095,984 A | 8/2000 | Amano et al. |
| 6,095,987 A | 8/2000 | Shmulewitz et al. |
| 6,117,075 A | 9/2000 | Barnea |
| 6,129,675 A | 10/2000 | Jay |
| 6,135,966 A | 10/2000 | Ko |
| 6,157,850 A | 12/2000 | Diab et al. |
| 6,159,157 A | 12/2000 | Archibald et al. |
| 6,161,038 A | 12/2000 | Schookin et al. |
| 6,171,257 B1 | 1/2001 | Weil et al. |
| 6,171,258 B1 | 1/2001 | Karakasoglu et al. |
| 6,186,954 B1 | 2/2001 | Narimatsu |
| 6,186,955 B1 | 2/2001 | Baura |
| 6,190,382 B1 | 2/2001 | Ormsby et al. |
| 6,196,974 B1 | 3/2001 | Miwa |
| 6,208,951 B1 | 3/2001 | Kumar et al. |
| 6,217,524 B1 | 4/2001 | Orr et al. |
| 6,227,196 B1 | 5/2001 | Jaffe et al. |
| 6,228,034 B1 | 5/2001 | Voss et al. |
| 6,229,856 B1 | 5/2001 | Diab et al. |
| 6,241,661 B1 | 6/2001 | Schluess et al. |
| 6,241,679 B1 | 6/2001 | Curran |
| 6,245,022 B1 | 6/2001 | Archibald et al. |
| 6,251,081 B1 | 6/2001 | Narimatsu |
| 6,263,222 B1 | 7/2001 | Diab et al. |
| 6,292,689 B1 | 9/2001 | Wallace et al. |
| 6,293,915 B1 | 9/2001 | Amano et al. |
| 6,299,582 B1 | 10/2001 | Brockway et al. |
| 6,325,761 B1 | 12/2001 | Jay |
| 6,332,867 B1 | 12/2001 | Chen et al. |
| 6,350,242 B1 | 2/2002 | Doten et al. |
| 6,361,501 B1 | 3/2002 | Amano et al. |
| 6,371,921 B1 | 4/2002 | Caro et al. |
| 6,393,311 B1 | 5/2002 | Edgar, Jr. et al. |
| 6,443,905 B1 | 9/2002 | Nissila et al. |
| 6,463,311 B1 | 10/2002 | Diab |
| 6,471,646 B1 | 10/2002 | Thede |
| 6,471,655 B1 | 10/2002 | Baura |
| 6,506,161 B2 | 1/2003 | Brockway et al. |
| 6,514,211 B1 | 2/2003 | Baura |
| 6,524,240 B1 | 2/2003 | Thede |
| 6,542,764 B1 | 4/2003 | Al-ali et al. |
| 6,561,986 B2 | 5/2003 | Baura et al. |
| 6,589,185 B1 | 7/2003 | Archibald et al. |
| 6,602,199 B2 | 8/2003 | Chen et al. |
| 6,602,201 B1 | 8/2003 | Hepp et al. |
| 6,606,511 B1 | 8/2003 | Ali et al. |
| 6,608,934 B2 | 8/2003 | Scheirer et al. |
| 6,626,839 B2 | 9/2003 | Doten et al. |
| 6,631,281 B1 | 10/2003 | Kastle |
| 6,643,530 B2 | 11/2003 | Diab et al. |
| 6,645,156 B2 | 11/2003 | Oka |
| 6,654,623 B1 | 11/2003 | Kastle |
| 6,658,277 B2 | 12/2003 | Wasserman |
| 6,684,090 B2 | 1/2004 | Ali et al. |
| RE38,476 E | 3/2004 | Diab et al. |
| 6,699,194 B1 | 3/2004 | Diab et al. |
| 6,767,328 B2 | 7/2004 | Kulik |
| 6,773,397 B2 | 8/2004 | Kelly |
| 6,783,498 B2 | 8/2004 | Sackner et al. |
| 6,810,277 B2 | 10/2004 | Edgar, Jr. et al. |
| 6,816,741 B2 | 11/2004 | Diab |
| 6,822,564 B2 | 11/2004 | Al-Ali |
| 6,826,419 B2 | 11/2004 | Diab et al. |
| 6,827,688 B2 | 12/2004 | Goto et al. |
| 6,852,083 B2 | 2/2005 | Caro et al. |
| 6,855,112 B2 | 2/2005 | Kao et al. |
| 6,863,652 B2 | 3/2005 | Huang et al. |
| 6,869,403 B2 | 3/2005 | Narimatsu et al. |
| 6,929,610 B2 | 8/2005 | Forstner |
| 6,931,269 B2 | 8/2005 | Terry |
| 6,996,427 B2 | 2/2006 | Ali et al. |
| 7,001,337 B2 | 2/2006 | Dekker |
| 7,003,339 B2 | 2/2006 | Diab et al. |
| 7,004,907 B2 | 2/2006 | Banet et al. |
| 7,020,507 B2 | 3/2006 | Scharf et al. |
| 7,035,679 B2 | 4/2006 | Addison et al. |
| 7,043,293 B1 | 5/2006 | Baura |
| 7,044,918 B2 | 5/2006 | Diab |
| 7,054,453 B2 | 5/2006 | Causevic et al. |
| 7,054,454 B2 | 5/2006 | Causevic et al. |
| 7,070,566 B2 | 7/2006 | Medero et al. |

(56) References Cited

U.S. PATENT DOCUMENTS

| | | | |
|---|---|---|---|
| 7,074,192 B2 | 7/2006 | Friedman et al. | |
| 7,079,035 B2 | 7/2006 | Bock et al. | |
| 7,079,888 B2 | 7/2006 | Oung et al. | |
| 7,087,025 B2 | 8/2006 | Baruch | |
| 7,171,269 B1 | 1/2007 | Addison et al. | |
| 7,173,525 B2 | 2/2007 | Albert | |
| 7,184,809 B1 | 2/2007 | Sterling et al. | |
| 7,203,267 B2 | 4/2007 | De Man et al. | |
| 7,215,984 B2 | 5/2007 | Diab et al. | |
| 7,215,986 B2 | 5/2007 | Diab et al. | |
| 7,221,971 B2 | 5/2007 | Diab et al. | |
| 7,225,013 B2 | 5/2007 | Geva et al. | |
| 7,252,636 B2 | 8/2007 | Brown | |
| 7,254,500 B2 | 8/2007 | Makeig et al. | |
| 7,289,835 B2 | 10/2007 | Mansfield et al. | |
| 7,320,030 B2 | 1/2008 | Brown | |
| 7,335,162 B2 | 2/2008 | Eide | |
| 7,376,238 B1 | 5/2008 | Rivas et al. | |
| 7,390,300 B2 | 6/2008 | Inukai et al. | |
| 7,390,301 B2 | 6/2008 | Skrabal et al. | |
| 7,393,327 B2 | 7/2008 | Inukai et al. | |
| 7,400,257 B2 | 7/2008 | Rivas | |
| 7,455,643 B1 | 11/2008 | Li et al. | |
| 7,481,772 B2 | 1/2009 | Banet | |
| 7,485,095 B2 | 2/2009 | Shusterman | |
| 7,515,949 B2 | 4/2009 | Norris | |
| 7,519,488 B2 | 4/2009 | Fu et al. | |
| 7,523,011 B2 | 4/2009 | Akiyama et al. | |
| 2002/0055680 A1* | 5/2002 | Miele et al. | 600/450 |
| 2003/0163057 A1 | 8/2003 | Flick et al. | |
| 2004/0167411 A1* | 8/2004 | Kolluri et al. | 600/490 |
| 2005/0043616 A1 | 2/2005 | Chinchoy | |
| 2005/0070774 A1* | 3/2005 | Addison et al. | 600/323 |
| 2005/0148885 A1 | 7/2005 | Tweed et al. | |
| 2005/0251344 A1 | 11/2005 | Appel et al. | |
| 2005/0261594 A1 | 11/2005 | Banet | |
| 2006/0009700 A1 | 1/2006 | Brumfield et al. | |
| 2006/0063992 A1 | 3/2006 | Yu et al. | |
| 2006/0063993 A1 | 3/2006 | Yu et al. | |
| 2006/0079945 A1 | 4/2006 | Libbus | |
| 2006/0206021 A1 | 9/2006 | Diab | |
| 2006/0209631 A1 | 9/2006 | Melese et al. | |
| 2006/0211930 A1 | 9/2006 | Scharf et al. | |
| 2006/0217614 A1 | 9/2006 | Takala et al. | |
| 2006/0217628 A1 | 9/2006 | Huiku | |
| 2006/0229519 A1 | 10/2006 | Fujiwara et al. | |
| 2006/0241975 A1 | 10/2006 | Brown | |
| 2006/0258921 A1 | 11/2006 | Addison et al. | |
| 2006/0265022 A1 | 11/2006 | John et al. | |
| 2006/0285736 A1 | 12/2006 | Brown | |
| 2006/0287603 A1 | 12/2006 | Bartnik et al. | |
| 2007/0021673 A1 | 1/2007 | Arbel et al. | |
| 2007/0066910 A1 | 3/2007 | Inukai et al. | |
| 2007/0073120 A1 | 3/2007 | Li et al. | |
| 2007/0073124 A1 | 3/2007 | Li et al. | |
| 2007/0083093 A1 | 4/2007 | Diab | |
| 2007/0118045 A1 | 5/2007 | Naghavi et al. | |
| 2007/0167694 A1 | 7/2007 | Causevic et al. | |
| 2007/0167851 A1 | 7/2007 | Vitali et al. | |
| 2007/0225582 A1 | 9/2007 | Diab et al. | |
| 2007/0249467 A1 | 10/2007 | Hong et al. | |
| 2007/0282212 A1 | 12/2007 | Sierra et al. | |
| 2008/0015451 A1 | 1/2008 | Hatib et al. | |
| 2008/0030468 A1 | 2/2008 | Ali et al. | |
| 2008/0033305 A1 | 2/2008 | Hatib et al. | |
| 2008/0045832 A1 | 2/2008 | McGrath | |
| 2008/0082018 A1 | 4/2008 | Sackner et al. | |
| 2008/0132798 A1 | 6/2008 | Hong et al. | |
| 2008/0214903 A1 | 9/2008 | Orbach | |
| 2008/0214942 A1 | 9/2008 | Oh et al. | |
| 2008/0242955 A1 | 10/2008 | Uutela et al. | |
| 2008/0243021 A1 | 10/2008 | Causevic et al. | |
| 2009/0048497 A1 | 2/2009 | Keren | |
| 2009/0112104 A1* | 4/2009 | Usuda et al. | 600/494 |

FOREIGN PATENT DOCUMENTS

| | | |
|---|---|---|
| EP | 0755221 | 1/1997 |
| EP | 0968681 A1 | 1/2000 |
| EP | 2055229 A1 | 5/2009 |
| GB | 2 356 250 | 5/2001 |
| GB | 2 356 251 | 5/2001 |
| GB | 2 356 252 | 5/2001 |
| JP | 03-225268 | 10/1991 |
| JP | 03-231630 | 10/1991 |
| JP | 06-142082 | 5/1994 |
| JP | 07-136136 | 5/1995 |
| JP | 09-084776 | 3/1997 |
| WO | 97/47236 A1 | 12/1997 |
| WO | 01/00087 A1 | 1/2001 |
| WO | WO-01/25802 | 4/2001 |
| WO | WO-01/62152 | 8/2001 |
| WO | 03/000125 A1 | 1/2003 |
| WO | WO-03/055395 | 7/2003 |
| WO | WO-2004/105601 | 12/2004 |
| WO | WO-2005/096170 | 10/2005 |
| WO | WO-2006/085120 | 8/2006 |

OTHER PUBLICATIONS

Addison, Paul, "The Little Wave with the Big Future," Physics World, Mar. 2004, pp. 35-39.

Bank, Alan J., Kaiser, Daniel R., "Smooth Muscle Relaxation: Effects on Arterial Compliance, Distensibility, Elastic modulus, and Pulse Wave Velocity," Hypertension, vol. 32, No. 2, Aug. 1998, pp. 356-359.

Berne, Robert M., Levy, Matthew N., eds., Physiology, 2nd edition, St. Louis, Mosby, 1988, pp. 357-681.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Finkelstein, Stanley M., Cohn, Jay N., "First- and Third-Order Models for Determining Arterial Compliance," Journal of Hypertension, vol. 10, supplement 6, Aug. 1992, pp. 511-514.

Fitchett, D., Bouthier, JD, Simon, A. Ch., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

Fletcher, Gerald F., ed., Cardiovascular Response to Exercise, Mt. Kisco, NY, Futura Publishing Co., 1994.

Fung, YC, Biomechanics: Circulation, 2nd Edition, New York, Springer, 1997.

Geddes, LA, Handbook of Blood Pressure Measurement, Clifton, New Jersey, Humana Press, 1991.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

Millasseau, Sandrine C, Guigui, Franck G, Kelly, Ronan P., Prasad, Krishna, Cockcroft, John R., Ritter, James M., Chowienczyk, Philip J., Noninvasive Assessment of the Digital Volume Pulse: Comparison with the Peripheral Pressure Pulse, Hypertension, vol. 36, No. 6, Dec. 2000, pp. 952-956.

Moyle, John TB, Hahn, CEW, Adams, Anthony P, Pulse Oximetry, Revised Edition, London, BMJ, 1998.

Nara, Andrew R., Burns, Michael P., Downs, W. Gregory, Blood Pressure, Redmond, Washington, SpaceLabs, 1989.

(56) References Cited

OTHER PUBLICATIONS

Nichols, Wilmer W., O'Rourke, Michael F., McDonald's Blood Flow in Arteries: Theoretic, Experimental, and Clinical Principles, 3rd Edition, Philadelphia, Lea & Febiger, 1990.

O'Rourke, Michael F., Gallagher, David E., "Pulse Wave Analysis," Journal of Hypertension, vol. 14, supplement 5, Dec. 1996, pp. S147-S157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, pp. 39-54, Feb. 1991.

Yamada, Michio, "Wavelet Analysis and Its Application," Journal of the Institute of Electronics, Information and Communication Engineers, vol. 76, No. 5, May 1993, pp. 518-528.

Young, Christopher C., Mark, Jonathan B., White, William, DeBree, Ashley, Vender, Jeffery S., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

International Search Report PCT/IB2010/001758, 4 pages, mailed Nov. 29, 2010.

\* cited by examiner

SYSTEMS AND METHODS FOR NON-INVASIVE DETERMINATION OF BLOOD PRESSURE

SUMMARY OF THE DISCLOSURE

The present disclosure relates to blood pressure determination techniques, and more particularly, relates to determining a patient's blood pressure from features of a wavelet transformation of a pressure signal obtained during an occlusion procedure.

Blood pressure is an important indicator of a patient's physiological status, and may be determined by several different techniques. Invasive techniques require the insertion of a monitoring catheter into a patient's artery, and may be accompanied by surgical complications such as hematoma, thrombosis and infection. Non-invasive blood pressure determination techniques include auscultatory and oscillometric techniques. Both of these techniques may involve monitoring a physiological signal while a blood channel, such as an artery or vessel, is variably occluded. A standard auscultatory technique begins by applying an external pressure to a patient's brachial artery via an occluding cuff wrapped around the upper arm. A trained technician then gradually decreases the applied pressure while listening to the occluded channel with a stethoscope for audible markers that indicate blood pressure features. Such techniques depend highly on the skill of the technician, require a quiet environment, and have been shown to exhibit systematic errors (e.g., underestimating systolic pressure). Additionally, the "auscultatory gap" exhibited by some patients may render these techniques difficult or unsuitable for such patients.

Rather than looking for audible markers, oscillometric blood pressure determination techniques monitor pressure oscillations sensed by an occluding device as the occlusion pressure varies. In one embodiment of an oscillometric technique, a variable pressure is applied to a blood channel via an occluding device such as a cuff or glove. As the pressure in the cuff is varied, a pressure sensor monitors the pressure exerted against the occluding device. This monitored pressure signal includes two components: the applied pressure signal as exerted by the device and an oscillation signal around the applied pressure signal caused by the patient's blood flow. It has been demonstrated that blood pressure measurements, such as mean arterial pressure, systolic pressure and diastolic pressure, may be determined by analyzing the oscillation signal component for characteristic points. For example, the pressure at which an oscillation signal reaches its peak amplitude may correspond to a patient's mean arterial pressure.

Existing blood pressure monitors that employ oscillometric methods suffer from a variety of limitations due to the techniques used for identifying these characteristic points in the oscillation signal. For example, existing monitors may only utilize the peak value of each individual oscillation in an oscillation signal, and therefore require many such oscillations (and a correspondingly long monitoring period) in order to obtain a measurement of sufficient accuracy. Since a patient's blood flow is impeded during the monitoring period, such devices may cause physical discomfort to a patient and may lead to severe physiological consequences. Additionally, existing techniques for obtaining the oscillation signal from the monitored pressure signal may require removing the applied pressure signal by applying a filter or some other destructive signal processing technique, which may distort the oscillation signal. Further, external noise and artifacts such as patient movement may interfere with the oscillation signal and may not be removed by traditional filtering techniques without deteriorating the underlying signal, which may lead to erroneous blood pressure determinations.

In some embodiments, the use of a transform may allow a pressure signal to be represented in a suitable domain such as, for example, a scalogram (in a time-scale domain) or a spectrogram (in a time-frequency domain). Features in a transformed pressure signal may then be used to extract the characteristic points in the oscillation signal. In an embodiment, a continuous wavelet transform applied to the pressure signal may allow ridges in the transformed signal to be identified. One or more of these ridges may correspond to an envelope of the oscillation signal, from which characteristic points may be extracted and blood pressure measurements determined.

The present disclosure relates to systems and methods for blood pressure determination using improved oscillometric techniques which are based on transformations of pressure signals, such as those that arise from a continuous wavelet transformation of a pressure signal. These systems and methods address the disadvantages of existing techniques.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Oscillometric blood pressure determination techniques may involve performing an occlusion procedure to obtain an oscillation signal. An occlusion procedure may include the following sequence of steps:
1. Using an occluding device, apply a pressure to a patient's body to occlude blood flow in a blood channel.
2. Vary the pressure applied by the occluding device and record a pressure signal.
3. Determine an oscillation signal from the pressure signal.

Figure 1:
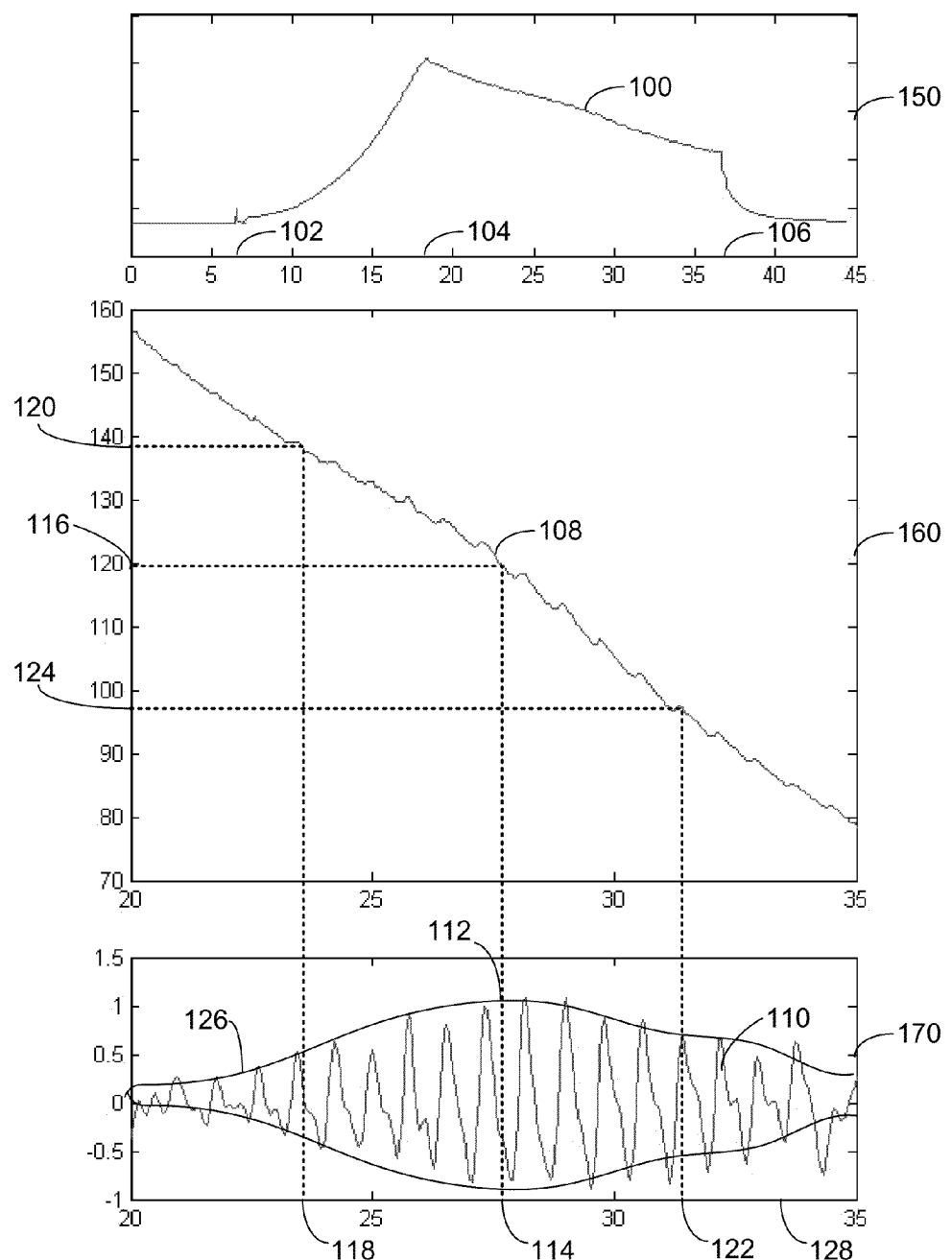
FIG. 1 depicts an illustrative pressure signal and an illustrative oscillation signal obtained during an occlusion procedure in accordance with an embodiment.

FIG. 1 depicts illustrative pressure signal 100 and illustrative oscillation signal 110 obtained during an occlusion procedure in accordance with an embodiment. In particular, plot 150 depicts an illustrative pressure signal 100 obtained by an automatic blood pressure cuff device applied to a volunteer patient during an occlusion procedure. Embodiments of such devices are described below with reference to FIGS. 2(a)-2(b). At time point 102 (which occurs approximately six seconds into the measurement), the pressure applied to the patient by the blood pressure cuff may begin to increase. The applied pressure may reach a peak at time point 104 (which occurs approximately 19 seconds into the measurement). This peak may correspond to an applied pressure of approximately 100-200 mm Hg, but may be more or less. Once the applied pressure has reached a peak at time point 104, the applied pressure may gradually decrease. This decrease may occur at a rate of less than 10 mm Hg per pulse, but may be faster. At time point 106 (which occurs approximately 37 seconds into the measurement), the pressure applied by the cuff to the patient may be released.

It is important to note that the particular pattern of increases and decreases in applied pressure illustrated in plot 150 is merely illustrative, and that the present disclosure includes embodiments in which the applied pressure follows a different sequence of increases and decreases. For example, the gradual decrease in the applied pressure between time points 104 and 106 occurs in an approximately linear manner. In an alternate embodiment, a pressure applied by an occluding device may increase to a peak value, then decrease in a non-linear manner. Such embodiments may include a stepped decrease, a variable-rate decrease, an exponential decrease, or any combination thereof. Rather than decreasing gradually, in an embodiment, an applied pressure may increase gradually to a maximum pressure. This increase may occur in a linear or non-linear manner, and may be followed by a release of pressure.

Plot 160 depicts a portion 108 of pressure signal 100 in greater detail. Portion 108 corresponds to the portion of pressure signal 100 between time points 104 and 106, during which the applied pressure may be decreasing from its maximum value. Portion 108 may be composed of two components: an applied pressure arising from the pressure applied by the occluding device, and an oscillatory pressure arising from the force exerted against the occluding device by a patient's blood flow.

Plot 170 depicts oscillation signal 110 which may be extracted from portion 108. Methods for extracting an oscillation signal from a pressure signal are discussed in additional detail below. In an embodiment, the amplitude of the oscillation signal may be used to determine blood pressure measurements, such as mean arterial pressure, systolic pressure and diastolic pressure.

In an embodiment, the value of pressure signal 100 at the time corresponding to the peak amplitude of oscillation signal 110 may provide a measurement of the mean arterial pressure. For example, in pressure signal portion 108 of plot 160, the mean arterial pressure 116 may be measured by identifying time point 114 in plot 170 corresponding to the peak amplitude 112 of oscillation signal 110, as characterized by oscillation envelope 126, and determining the value 116 of pressure signal 100 at time point 114.

In an embodiment, at least one of a systolic and a diastolic blood pressure may be determined from oscillation signal 110. In an embodiment, the value of the pressure signal 100 at a time corresponding to a particular amplitude of the oscillation signal 110 may provide a measurement of the systolic blood pressure. This particular amplitude may be related to the peak amplitude by a scale factor (e.g., a multiplicative factor). This scale factor may fall in the approximate range 0.5-0.55. For example, plot 170 illustrates time point 118, at which the amplitude of oscillation signal 110, as characterized by oscillation envelope 126, may be approximately equal to the peak amplitude multiplied by a scale factor of 0.5. A patient's systolic blood pressure may be measured by identifying the value 120 of the pressure signal portion 108 at time point 118. Time point 118 (at which systolic blood pressure may be measured from pressure signal 100) may be distinguished from another time at which the oscillation amplitude is approximately equal to the peak amplitude scaled by 0.5 (e.g., at time 128) by known physiological constraints. For example, systolic pressure is known to be greater than mean arterial pressure, which may allow time points at which the pressure signal 100 is less than the mean arterial pressure to be ignored when locating time points corresponding to systolic pressure.

In an embodiment, the value of the pressure signal 100 at a time corresponding to a particular amplitude of oscillation signal 110 may provide a measurement of the diastolic blood pressure. This particular amplitude may be related to the peak amplitude by a scale factor (e.g., a multiplicative factor). This scale factor may fall in the approximate range 0.7-0.85. For example, plot 170 illustrates time point 122, at which the amplitude of oscillation signal 110, as characterized by oscillation envelope 126, may be approximately equal to the peak amplitude multiplied by a scale factor of 0.8. A patient's diastolic blood pressure may be measured by identifying the value 124 of the pressure signal 100 at time point 122. The time point 122 (at which diastolic blood pressure may be measured from pressure signal 100) may be distinguished from another time at which the oscillation amplitude is approximately equal to the peak amplitude scaled by 0.8 by known physiological constraints. For example, diastolic pressure is known to be less than mean arterial pressure, which may allow time points at which the pressure signal 100 is greater than the mean arterial pressure to be ignored when locating time points corresponding to diastolic pressure.

The scale factor ranges presented above are merely illustrative. Any other suitable scale factor range or ranges may be used in the context of the present disclosure, including any suitable scale factor range or ranges described in the literature.

In an embodiment, the mean arterial pressure may not correspond to the peak amplitude of the oscillation signal, but may correspond to a time at which the oscillation signal has an amplitude that is related to the peak amplitude by a scale factor (e.g., a multiplicative factor in the approximate range 0.9-1). Additionally, mean arterial pressure $P_m$, systolic pressure $P_s$ and diastolic pressure $P_d$ may be related according to the following relationship:

$$P_m = P_d + \frac{P_s - P_d}{3}. \qquad (1)$$

In an embodiment, any two of the mean arterial pressure, systolic pressure and diastolic pressure may be determined by any of the oscillometric techniques described herein, and the third pressure may be determined from the relationship of Eq. 1. In an embodiment, the relationship of Eq. 1 may be used to validate or adjust the determination of a blood pressure measurement using an oscillometric technique. Other relationships may be used to determine one or more of mean arterial pressure $P_m$, systolic pressure $P_s$ and diastolic pressure $P_d$, including relationships which are based at least in part on a patient's pulse rate.

As illustrated in the above examples, when performing an oscillometric blood pressure determination, it may be important to accurately identify the amplitude of an oscillation signal. In an embodiment, the amplitude of an oscillation signal is characterized by an envelope of the oscillation signal, such as oscillation envelope 126 of oscillation signal 110 as depicted in FIG. 1. The oscillometric blood pressure determination techniques disclosed herein which identify an envelope may advantageously allow an oscillation amplitude to be determined between local maxima of an oscillation signal, thereby providing additional pressure resolution and decreasing the time required to obtain an accurate measurement. In an embodiment, an oscillation envelope may be determined from a transformation of a pressure signal such as pressure signal 100. For example, an oscillation envelope may be determined by applying a band-pass or other suitable filter to pressure signal 100. In another example, a Hilbert transform may be applied to pressure signal 100 to extract an oscillation envelope.

In an embodiment, an oscillation envelope may be determined by performing a wavelet transformation on a pressure signal such as pressure signal 100. Features of a transformed pressure signal may allow the determination of an oscillation envelope, and from the oscillation envelope, blood pressure measurements may be made. Embodiments of systems and methods for determining an oscillation envelope from a transformed signal are described in detail below with reference to FIGS. 2-7.

Figure 2A:
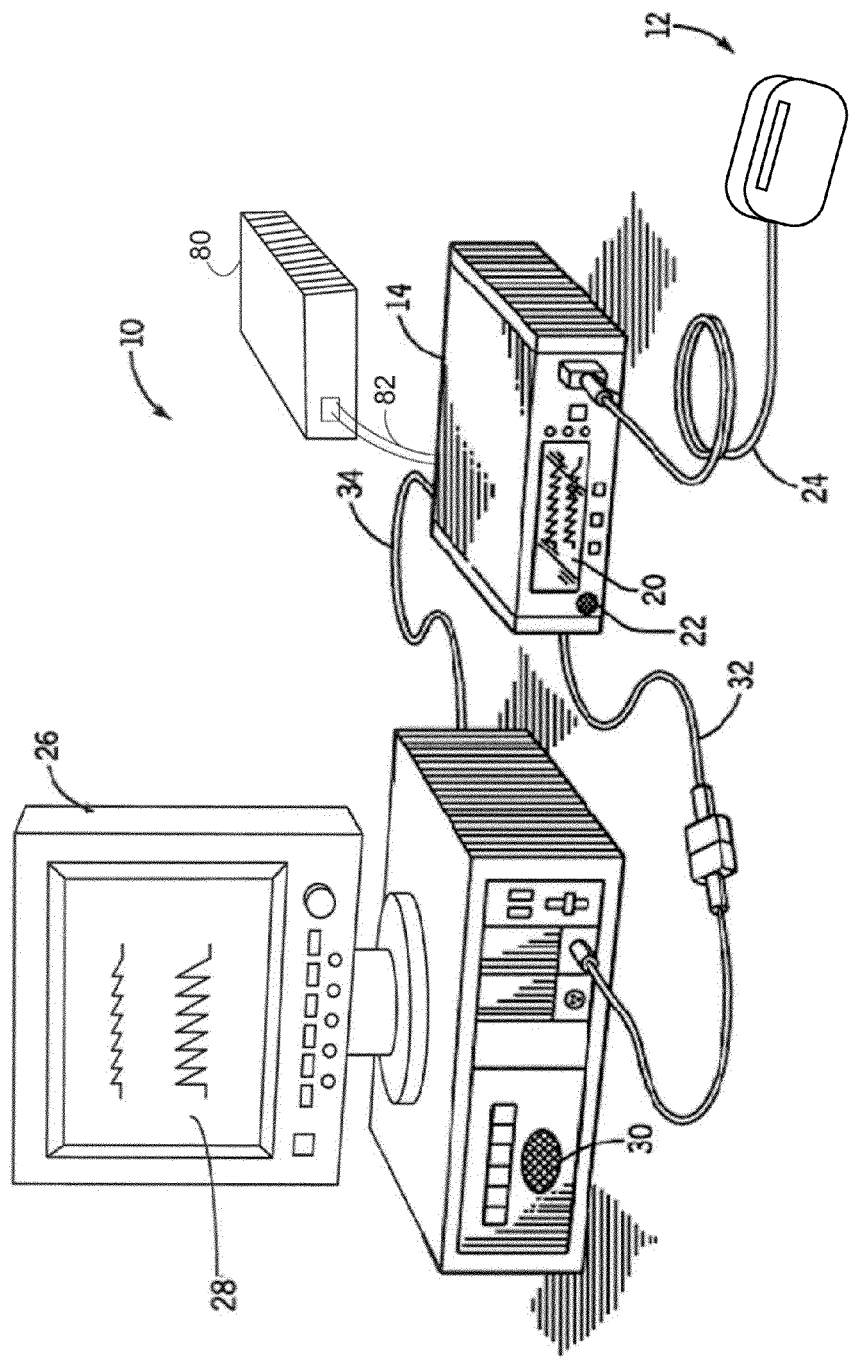
FIG. 2(a) shows an illustrative blood pressure monitoring system in accordance with an embodiment.

FIG. 2(a) is a perspective view of an embodiment of a blood pressure monitoring system 10. In an embodiment, blood pressure monitoring system 10 is implemented as part of a patient monitoring system. System 10 may include occluding device 12 and monitor 14.

Occluding device 12 may include any device that is capable of applying a force or pressure to a blood channel to impede the flow of blood. Such a device may exert a pressure on a patient's skin to occlude flow in a blood channel beneath the skin. In an embodiment, an occluding device may include any one or more of the following: a pressure sleeve, a pressure mitten, a finger cuff, a wrist cuff, an arm cuff, a thigh cuff, a leg cuff, an ankle cuff, and a neck pad. Occluding device 12 may be stationary or may be portable. Various embodiments of occluding device 12 are discussed below with reference to FIG. 2(b).

In an embodiment, occluding device 12 may be coupled to and draw its power from monitor 14 as shown. In another embodiment, occluding device 12 may be wirelessly connected to monitor 14 and include its own battery or similar power supply (not shown). Monitor 14 may be configured to calculate physiological parameters based at least in part on data received from occluding device 12 relating to pressure.

In an alternative embodiment, the calculations may be performed on the occluding device itself and the result of the pressure reading may be passed to monitor 14. Further, monitor 14 may include a display 20 configured to display a patient's physiological parameters, such as a blood pressure measurement, or information about the system. In the embodiment shown, monitor 14 may also include a speaker 22 to provide an audible sound that may be used in various other embodiments, such as, for example, sounding an audible alarm in the event that a patient's physiological parameters are not within a predefined normal range.

In an embodiment, occluding device 12 may be communicatively coupled to monitor 14 via a cable 24. However, in other embodiments, a wireless transmission device (not shown) or the like may be used instead of or in addition to cable 24.

In the illustrated embodiment, blood pressure monitoring system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patient's blood pressure generated by monitor 14 on display 28.

Monitor 14 may be communicatively coupled to multi-parameter patient monitor 26 via a cable 32 or 34 that is coupled to a sensor input port or a digital communications port, respectively, and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

System 10 may optionally include calibration device 80. Calibration device 80, which may be powered by monitor 14 via a cable 82, a battery, or by a conventional power source such as a wall outlet, may include any suitable physiological signal calibration device. For example, calibration device 80 may take the form of any invasive or non-invasive physiological monitoring or measuring system used to generate reference physiological measurements for use in calibrating a monitoring device. For example, calibration device 80 may take the form of a blood pressure calibration device, and may include, for example, an aneroid or mercury sphygmomanometer and occluding cuff, a pressure sensor inserted directly into a suitable artery of a patient, an oscillometric device or any other device or mechanism used to sense, measure, determine, or derive a reference blood pressure measurement. In some embodiments, calibration device 80 may include a manual input device (not shown) used by an operator to manually input reference physiological measurements obtained from some other source (e.g., an external invasive or non-invasive physiological measurement system). Calibration device 80 may be communicatively coupled to monitor 14 via cable 82, and/or may communicate wirelessly (not shown). In an embodiment, calibration device 80 may be directly connected to or integrated with occluding device 12 (not shown). In an embodiment, calibration device 80 may provide a blood pressure measurement calibration. Such a calibration device may determine blood pressure using any of a number of techniques, including invasive techniques (which may involve an arterial line), auscultatory techniques (which may involve a contact microphone), or any other suitable technique, or any combination of techniques.

In an embodiment, calibration device 80 may be a pulse oximeter. Techniques for obtaining blood pressure measurements from oximetry data are described in more detail in, for example, co-pending, commonly assigned U.S. patent application Ser. No. 12/242,867, filed Sep. 30, 2008, entitled "SYSTEMS AND METHODS FOR NON-INVASIVE CONTINUOUS BLOOD PRESSURE DETERMINATION" and co-pending, commonly assigned U.S. patent application Ser. No. 12/242,238, filed Sep. 30, 2008, entitled "LASER SELF-MIXING SENSORS FOR BIOLOGICAL SENSING," which are both incorporated by reference herein in their entireties. In an embodiment, calibration device 80 includes a laser Doppler sensor.

Calibration device 80 may also access reference measurements stored in memory (e.g., RAM, ROM, or a storage device). As described in more detail below, the reference measurements generated or accessed by calibration device 80 may be updated in real-time, resulting in a continuous source of reference measurements for use in continuous or periodic calibration. Alternatively, reference measurements generated or accessed by calibration device 80 may be updated periodically, and calibration may be performed on the same periodic cycle. In the depicted embodiments, calibration device 80 is connected to monitor 14 via cable 82. In other embodiments, calibration device 80 may be a stand-alone device that may be in wireless communication with monitor 14 or occluding device 12. Reference measurements may then be wirelessly communicated to monitor 14 or occluding device 12 for use in calibration. In still other embodiments, calibration device 80 is completely integrated within monitor 14. For example, in some embodiments, calibration device 80 may access reference measurements from a relational database stored within calibration device 80, monitor 14, or multi-parameter patient monitor 26. Calibration device 80 may be responsive to an electronic recalibration signal, which may initiate the calibration of monitor 14 or occluding device 12 or may communicate recalibration information to calibration device 80 (e.g., a recalibration schedule). Calibration may be performed at any suitable time (e.g., once initially after monitoring begins) or on any suitable schedule (e.g., a periodic or event-driven schedule).

Figure 2B:
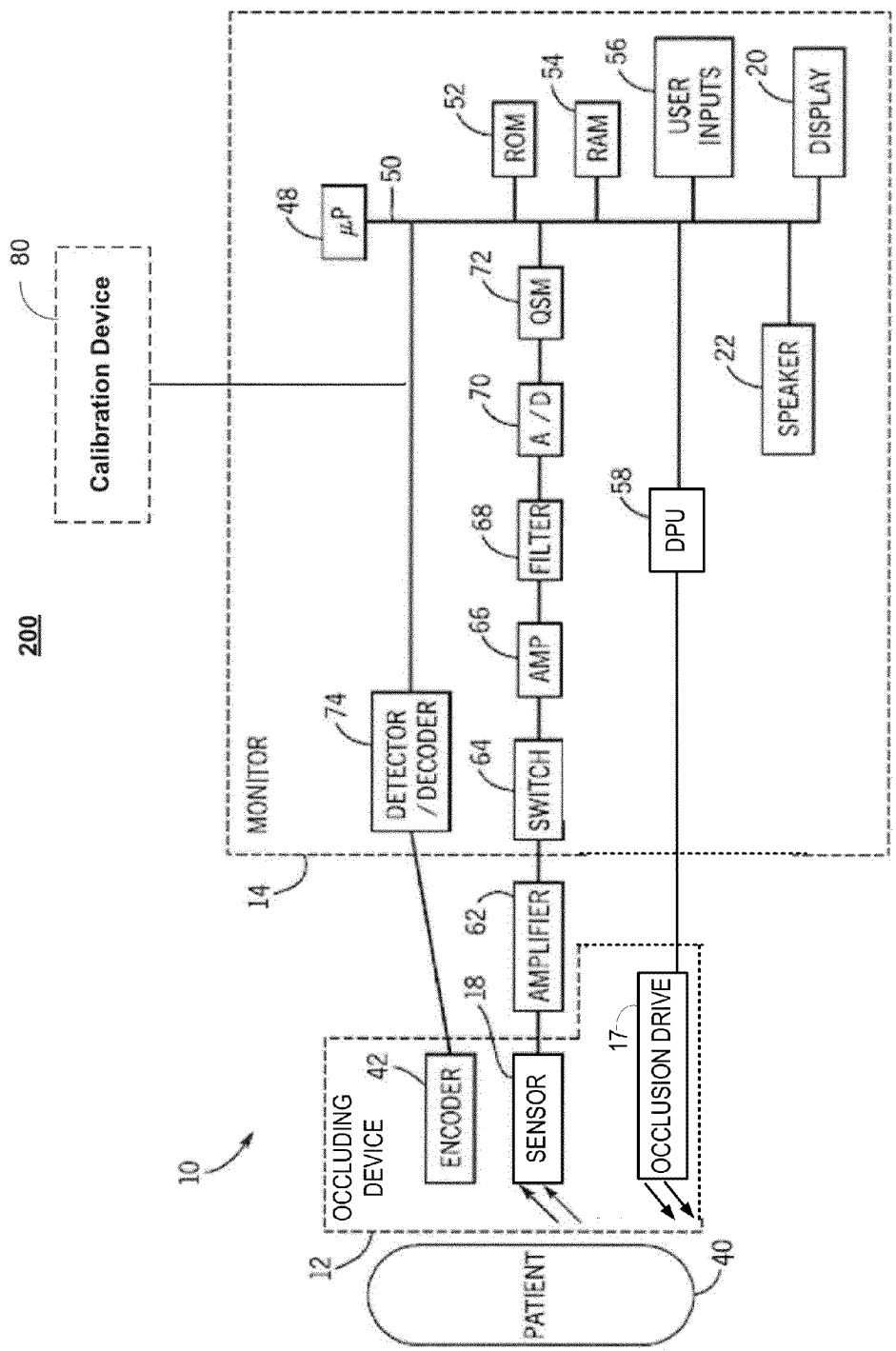
FIG. 2(b) is a block diagram of an illustrative blood pressure monitoring system coupled to a patient in accordance with an embodiment.

FIG. 2(b) is a block diagram of a blood pressure monitoring system, such as blood pressure monitoring system 10 of FIG. 2(a), which may be coupled to a patient 40 in accordance with an embodiment. Certain illustrative components of occluding device 12 and monitor 14 are illustrated in FIG. 2(b).

Occluding device 12 may include occlusion drive 17 and sensor 18. Occlusion drive 17 may control and/or apply an occluding pressure to a patient. For example, occlusion drive 17 may include a pneumatic drive which uses a fluid system (e.g., water-driven, oil-driven, or air-driven) to apply a pressure to a patient. In an embodiment, occluding device 12 includes adjustable air bladders that are capable of applying a pressure to a patient for blood flow occlusion. Occlusion drive 17 may increase and decrease the pressure to a patient in a stepped manner, in a continuous manner, or a combination of the two. Occlusion drive 17 may be responsive to control signals within occluding device 12, or may receive control signals from monitor 14 or another component of system 10.

Sensor 18 of occluding device 12 may detect a signal that carries information about the pressure exerted by a patient's blood flow. Sensor 18 may include any suitable pressure sensor, including any one or more of a fiber optic sensor, a mechanical deflection sensor, a strain gauge, a mercury column, a piezoelectric transducer, a microelectromechanical sensor, a variable capacitance sensor, any pressure transducer, or any combination thereof. In an embodiment, sensor 18 may detect the pulsatile force exerted on the walls of an artery using, for example, a piezoelectric transducer. Sensor 18 may produce an electrical signal, an audio signal, an optical signal, or any combination thereof. The components of occluding device 12, such as occlusion drive 17 and sensor 18, may each be analog, digital, or a combination of the two.

Occluding device 12 may be fully-automatic, semi-automatic, or manually operable. For example, occluding device 12 may be capable of performing an occlusion procedure in which an air bladder is manually inflated by a user or care provider, but deflation and/or data collection via sensor 18 is automated. In an embodiment, occlusion drive 17 and sensor 18 are separably operable, and may each be connected to monitor 14. In an embodiment, an occluding device may be capable of operation with interchangeable components. Multiple occluding cuffs may be capable of operation with occluding device 12, which may be selectively utilized depending upon the area of the patient's body to which the cuff is to be applied and/or a patient's physical characteristics. For example, the accuracy of blood pressure measurements arising from an arm cuff may depend on the ratio of the cuff width to the circumference of a patient's arm, and thus different cuffs may be preferably utilized with different patients. In an embodiment, occluding device 12 may not include an occlusion drive 17 and may include a manual pressure applied to a patient's blood channel by a care provider (e.g., by squeezing a finger or wrist), with a sensor (e.g., sensor 18) configured and located to detect the applied pressure and the oscillation signal.

In an embodiment, encoder 42 may contain information about occluding device 12, such as what type of occluding device it is (e.g., the intended placement of the occluding device on the patient's body, the type of pressure or force sensor included in the occluding device). This information may be used by monitor 14 to select appropriate computational techniques, lookup tables and/or calibration coefficients stored in monitor 14 for calculating the patient's physiological parameters. Encoder 42 may, for instance, be a coded resistor which stores values corresponding to the type of occluding device 12. In another embodiment, encoder 42 may include a memory on which occluding device information may be stored for communication to monitor 14.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter computation techniques.

In an embodiment, signals from occluding device 12 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a drive processing unit (DPU) 58 may provide control signals to occlusion drive 17, which may control the occluding force applied to the patient by occluding device 12. The occlusion procedure applied by occluding device 12 and controlled by DPU 58 and occlusion drive 17 may be based at least in part on characteristics of patient 40. For example, if patient 40 has had past blood pressure readings that are relatively low, the maximum pressure applied by occluding device 12 at a subsequent measurement may be less than the maximum pressure applied to another patient with past blood pressure readings that are relatively high.

The received signal from sensor 18 may be passed through an amplifier 66, a filter 68, and an analog-to-digital converter 70. In an embodiment, filter 68 may be a low-pass filter. In an embodiment, filter 68 may be a band-pass filter. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for each of multiple sensors communicably coupled to monitor 14.

In an embodiment, microprocessor 48 may determine the patient's physiological parameters, such as blood pressure, using various techniques and/or look-up tables based on the value of the signal from sensor 18. Signals corresponding to information about patient 40 may be transmitted from encoder 42 to decoder 74. These signals may include, for example, encoded information relating to patient characteristics. Decoder 74 may translate these signals to enable the microprocessor to determine thresholds based on computational techniques or look-up tables stored in ROM 52. User inputs 56 may be used to enter information about the patient, such as age, weight, height, diagnosis, medications, treatments, and so forth. Such information may be stored in a suitable memory (e.g., RAM 54) and may allow monitor 14 to determine, for example, patient-specific threshold ranges in which the patient's physiological parameter measurements should fall and to enable or disable additional physiological parameter computational techniques. In an embodiment, display 20 may exhibit a list of values which may generally apply to the patient, such as, for example, age ranges or medication families, which a user may select using user inputs 56.

A pressure signal through the tissue can be degraded by noise, among other sources. One source of noise is electromagnetic coupling from other electronic instruments. Movement of the patient also introduces noise and affects the signal. For example, the contact between sensor 18 and the skin, or occluding device 12 and the skin, can be temporarily disrupted when movement causes either to move away from the skin.

Noise (e.g., from patient movement) can degrade a pressure signal relied upon by a physician without the physician's awareness. This is especially true if the monitoring of the patient is remote, the motion is too small to be observed, or the doctor is watching the instrument or other parts of the patient and not the sensor site. Processing pressure signals may involve operations that reduce the amount of noise present in the signals or otherwise identify noise components in order to prevent them from affecting measurements of physiological parameters derived from the pressure signals.

In one embodiment, a pressure signal may be transformed using a continuous wavelet transform. Information derived from the transform of the pressure signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t) \psi^* \left( \frac{t-b}{a} \right) dt \qquad (2)$$

where $\psi^*(t)$ is the complex conjugate of the wavelet function $\psi(t)$, a is the dilation parameter of the wavelet and b is the location parameter of the wavelet. The transform given by Eq. 2 may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \qquad (3)$$

where '| |' is the modulus operator. The scalogram may be rescaled for useful purposes. One common rescaling is defined as $$S_R(a, b) = \frac{|T(a, b)|^2}{a} \qquad (4)$$

and is useful for defining ridges in wavelet space when, for example, the Morlet wavelet is used. Ridges are defined as a locus of points of local maxima in the plane. A ridge associated with only the locus of points of local maxima in the plane is labeled a "maxima ridge." Also included as a definition of a ridge herein are paths displaced from the locus of the local maxima. Any other suitable definition of a ridge may be employed in the methods disclosed herein.

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, a "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform T(a, b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram."

A scale, which may be interpreted as a representative temporal period, may be converted to a characteristic frequency of the wavelet function. The characteristic frequency associated with a wavelet of arbitrary a scale is given by $$f = \frac{f_c}{a} \qquad (5)$$

where $f_c$ is the characteristic frequency of the mother wavelet (i.e., at a=1) and becomes a scaling constant, and f is the representative or characteristic frequency for the wavelet at arbitrary scale a.

Any suitable wavelet function may be used in connection with the present disclosure. One of the most commonly used complex wavelets, the Morlet wavelet, is defined as $$\psi(t) = \pi^{-1/4}(e^{i2\pi f_0 t} - e^{-(2\pi f_0)^2/2})e^{-t^2/2} \qquad (6)$$

where $f_0$ is the central frequency of the mother wavelet. The second term in the parentheses is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{\frac{1}{4}}} e^{i2\pi f_0 t} e^{-t^2/2}. \qquad (7)$$

This wavelet is a complex wave within a scaled Gaussian envelope. While both definitions of the Morlet wavelet are included herein, the function of Eq. 7 is not strictly a wavelet as it has a non-zero mean (i.e., the zero frequency term of its corresponding energy spectrum is non-zero). However, it will be recognized by those skilled in the art that Eq. 7 may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of pressure signals may be used to provide clinically useful information within a medical device (e.g., about blood pressure).

Figures 3A, 3B:
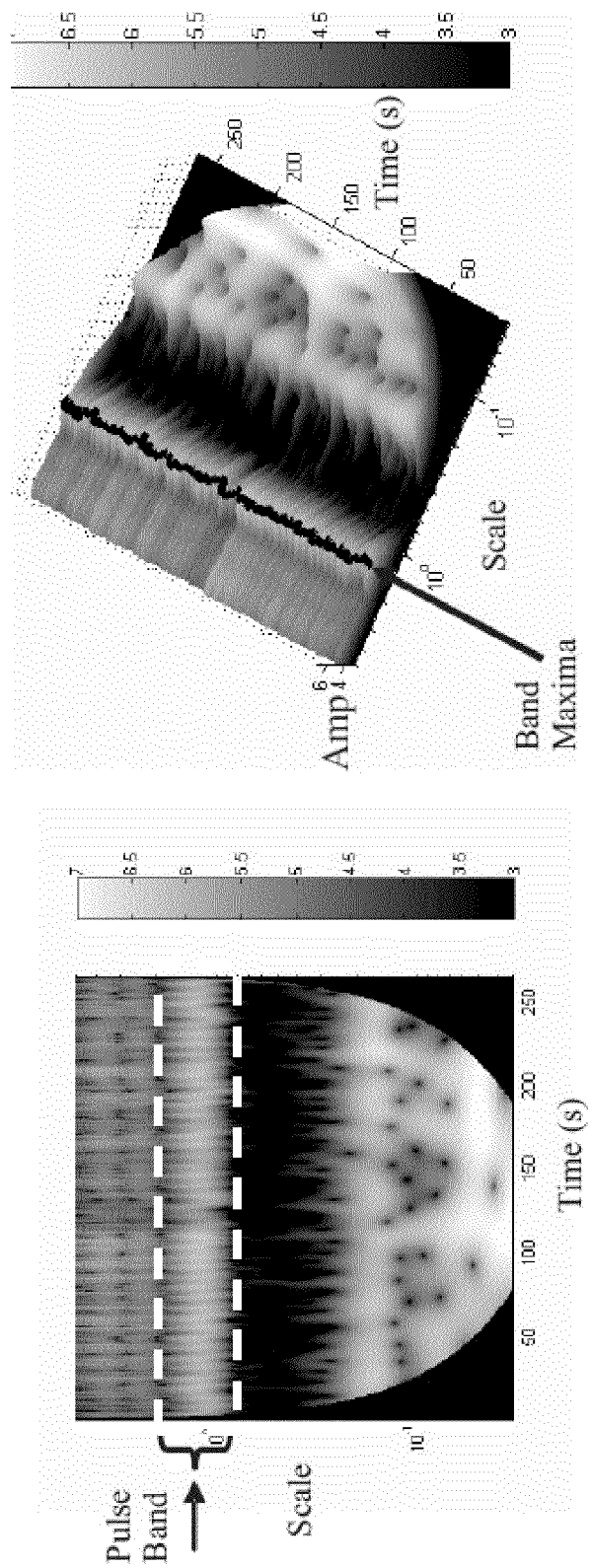
FIGS. 3(a) and 3(b) show illustrative views of a scalogram derived from a physiological signal in accordance with an embodiment.

Pertinent repeating features in a signal give rise to a time-scale band in wavelet space or a rescaled wavelet space. For example, the pulse component of a pressure signal produces a dominant band in wavelet space at or around the pulse frequency. FIGS. 3(a) and 3(b) show two views of an illustrative scalogram derived from a physiological signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in Eq. 4, the ridges found in wavelet space may be related to the instantaneous frequency of the signal. In this way, the pulse rate may be obtained from the pressure signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
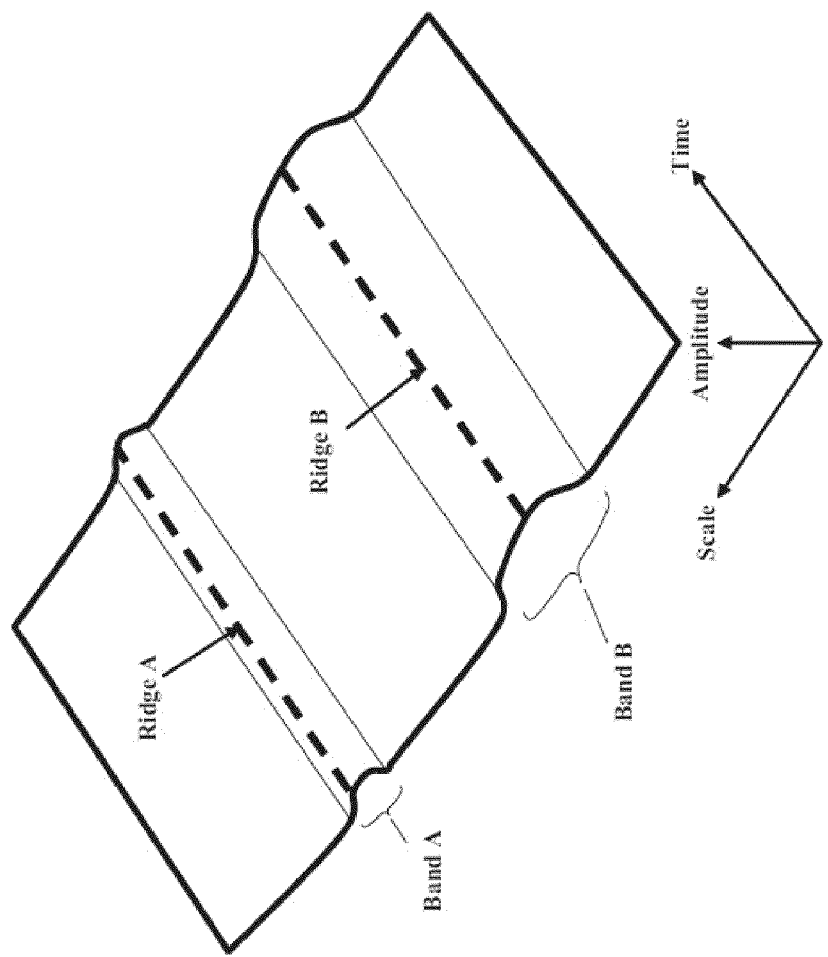
FIG. 3(c) shows an illustrative scalogram derived from a signal containing two pertinent components in accordance with an embodiment.
Figure 3D:
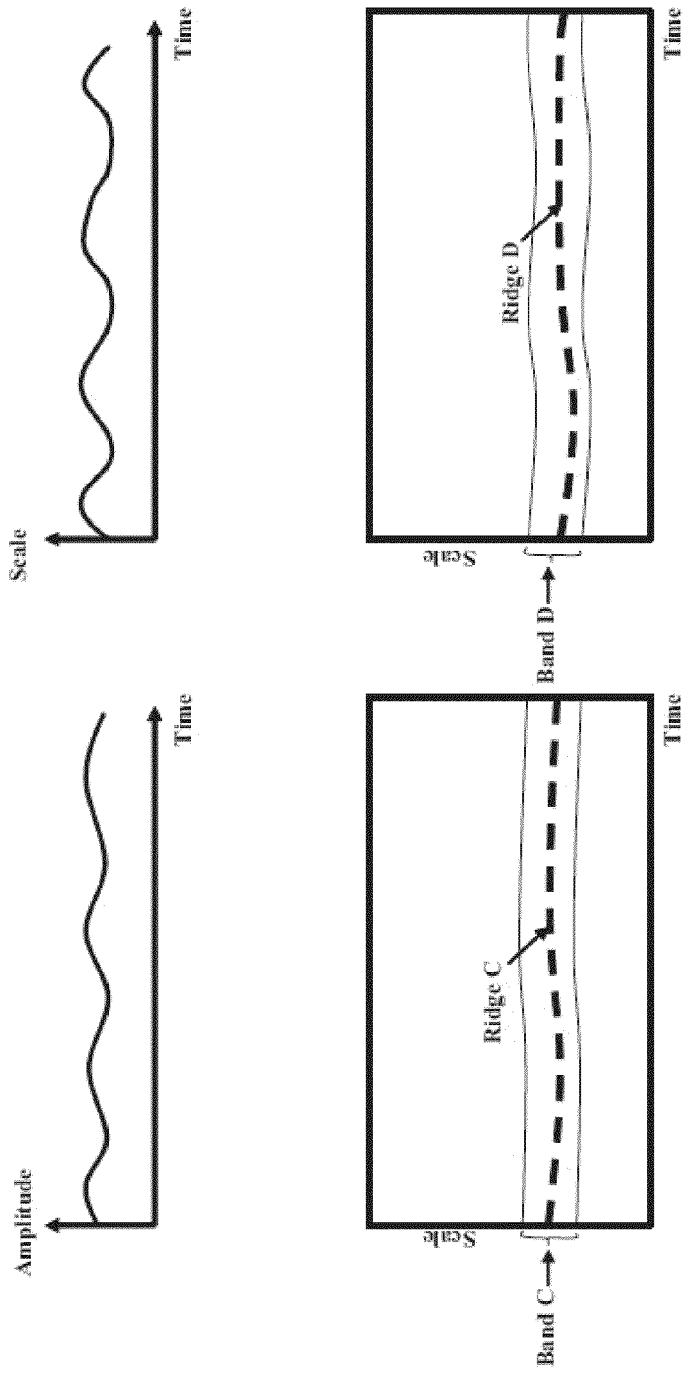
FIG. 3(d) shows an illustrative schematic of signals associated with a ridge in FIG. 3(c) and illustrative schematics of a further wavelet decomposition of derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary: varying in scale, amplitude, or both, over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In an embodiment, a band ridge is defined as the locus of the peak values of these bands with respect to scale. For purposes of discussion, it may be assumed that band B contains the signal information of interest. Band B will be referred to as the "primary band." In addition, it may be assumed that the system from which the signal originates, and from which the transform is subsequently derived, exhibits some form of coupling between the signal components in band A and band B. When noise or other erroneous features are present in the signal with similar spectral characteristics of the features of band B, the information within band B can become ambiguous (i.e., obscured, fragmented or missing). In this case, the ridge of band A (referred to herein as "ridge A") may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b, in accordance with $$x(t) = \frac{1}{C_g} \int_{-\infty}^{\infty} \int_{0}^{\infty} T(a,b) \frac{1}{\sqrt{a}} \psi\left(\frac{t-b}{a}\right) \frac{da\,db}{a^2}, \qquad (8)$$

which may also be written as $$x(t) = \frac{1}{C_g} \int_{-\infty}^{\infty} \int_{0}^{\infty} T(a,b) \psi_{a,b}(t) \frac{da\,db}{a^2}, \qquad (9)$$

where $C_g$ is a scalar value known as the admissibility constant. It is wavelet-type dependent and may be calculated in accordance with $$C_g = \int_0^\infty \frac{|\hat{\psi}(f)|^2}{f} df. \qquad (10)$$

Figure 3E:
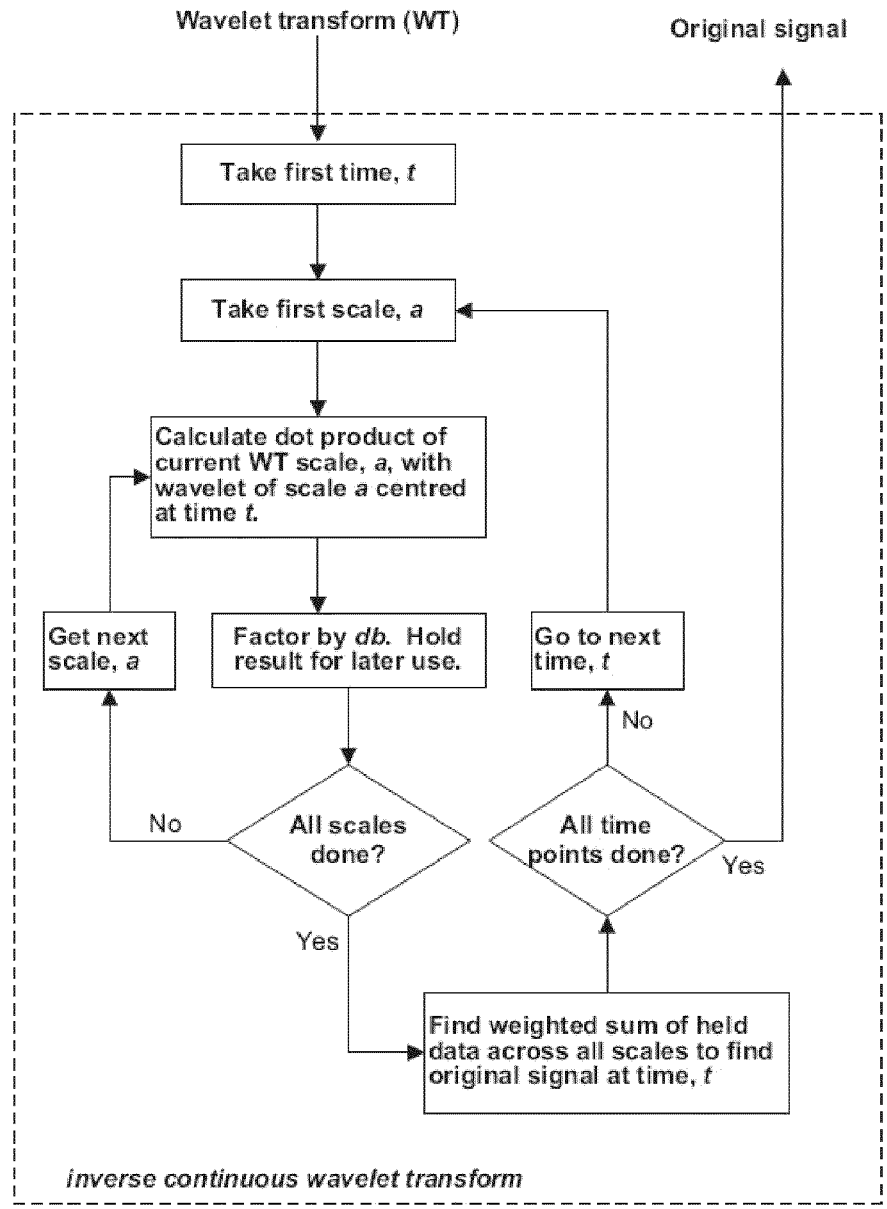
FIGS. 3(e) and 3(f) are flow charts of illustrative steps involved in performing an inverse continuous wavelet transform in accordance with an embodiment.
Figure 3F:
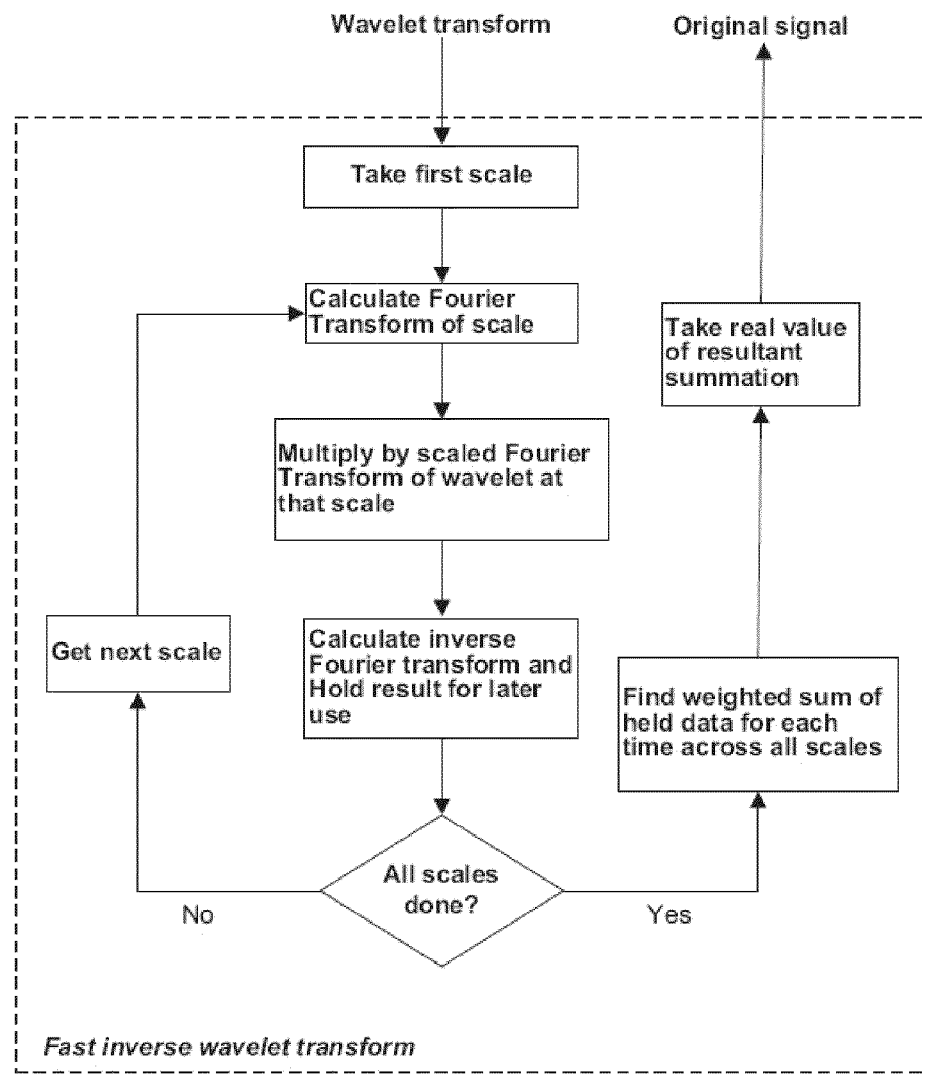

FIG. 3(e) is a flow chart of illustrative steps that may be taken to perform an inverse continuous wavelet transform in accordance with the above discussion. An approximation to the inverse transform may be made by considering Eq. 8 to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

The present disclosure relates to methods and systems for processing a signal using the above mentioned techniques and analyzing the results of the techniques to determine blood pressure. In an embodiment, blood pressure may be determined by analyzing one or more ridges in a scalogram of a pressure signal obtaining during an occlusion procedure. The one or more ridges may provide an oscillation envelope, to which oscillometric blood pressure techniques may be applied, such as identifying characteristic points as discussed above with reference to FIG. 1.

The methods for determining blood pressure described in this disclosure may be implemented on any one or more of a multitude of different systems and apparatuses through the use of human-readable or machine-readable information. For example, the methods described herein may be implemented using machine-readable computer code and executed on a computer system that is capable of reading the computer code. An exemplary system that is capable of determining blood pressure is depicted in FIG. 4.

Figure 4:
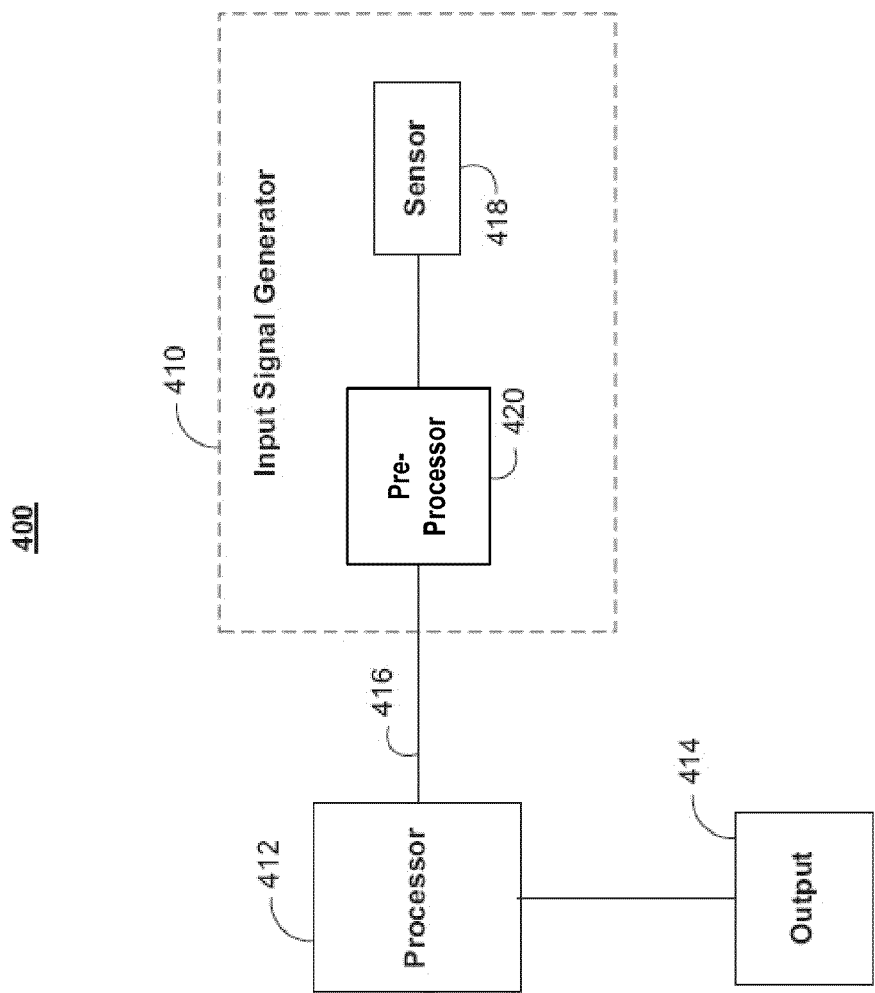
FIG. 4 is a block diagram of an illustrative continuous wavelet processing system in accordance with an embodiment.

FIG. 4 is an illustrative continuous wavelet processing system in accordance with an embodiment. In an embodiment, input signal generator 410 generates an input signal 416. As illustrated, input signal generator 410 may include pre-processor 420 coupled to sensor 418, which may provide as input signal 416, a pressure signal. It will be understood that input signal generator 410 may include any suitable signal source, signal generating data, signal generating equipment, or any combination thereof to produce signal 416. Signal 416 may be a single signal, or may be multiple signals transmitted over a single pathway or multiple pathways. For example, signal 416 may include information from multiple sensors embedded in occluding device 12.

Pre-processor 420 may apply one or more signal processing techniques to the signal generated by sensor 418. For example, pre-processor 420 may apply a pre-determined transformation to the signal provided by the sensor 418 to produce an input signal 416 that can be appropriately interpreted by processor 412. Pre-processor 420 may also perform any of the following operations to the signal provided by sensor 418: reshaping the signal for transmission; multiplexing the signal; modulating the signal onto carrier signals; compressing the signal; encoding the signal; and filtering the signal.

In an embodiment, signal 416 may be coupled to processor 412. Processor 412 may be any suitable software, firmware, and/or hardware, and/or combination thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may, for example, be configured of analog electronic components. Processor 412 may perform the calculations associated with the continuous wavelet transforms of the present disclosure as well as the calculations associated with any suitable interrogations of the transforms. For example, processor 412 may perform a ridge detection technique as described herein. Processor 412 may identify characteristic points in an oscillation envelope to determine blood pressure measurements. Processor 412 may perform any suitable signal processing of signal 416 to filter signal 416, such as any suitable band-pass filtering, adaptive filtering, closed-loop filtering, and/or any other suitable filtering, and/or any combination thereof. Processor 412 may also receive input signals from additional sources (not shown). For example, processor 412 may receive an input signal containing information about calibrations. These additional input signals may be used by processor 412 in any of the calculations or operations it performs in accordance with the blood pressure monitoring system 10.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof. In an embodiment, output 414 will be stored in a memory device or recorded in another physical form for future, further analysis.

It will be understood that system 400 may be incorporated into system 10 (FIGS. 2(a)-2(b)) in which, for example, input signal generator 410 may be implemented as parts of occluding device 12 and monitor 14, and processor 412 may be implemented as part of monitor 14. In some embodiments, portions of system 400 may be configured to be portable. For example, all or a part of system 400 may be embedded in a small, compact object carried with or attached to the patient (e.g., a watch, other piece of jewelry, or cellular telephone). In such embodiments, a wireless transceiver (not shown) may also be included in system 400 to enable wireless communication with other components of system 10. As such, system 10 may be part of a fully portable and continuous patient monitoring solution.

In some embodiments, in order to determine blood pressure, processor 412 may first transform the signal into any suitable domain, for example, a Fourier, Laplace, wavelet, Z-transform, scale, time, time-spectral, time-scale domain, a domain based on any suitable basis function, any other transform space, or any combination thereof. Processor 412 may further transform the original and/or transformed signals into any of the suitable domains as necessary. Processor 412 may represent the original or transformed signals in any suitable way, for example, through a two-dimensional representation or three-dimensional representation, such as a spectrogram or scalogram.

After processor 412 represents the signals in a suitable fashion, processor 412 may then find and analyze selected features in the signal representation of signal 416 to determine blood pressure. Selected features may include the value, weighted value, or change in values with regard to energy, amplitude, frequency modulation, amplitude modulation, scale modulation, differences between features (e.g., distances between ridge amplitude peaks within a time-scale band), or any combination thereof.

For example, selected features may include features in a time-scale band in wavelet space or a rescaled wavelet space described above. As an illustrative example, the projection of a pulse band ridge onto the time-amplitude plane or time-modulus plane may be indicative of the envelope of the oscillation signal obtained during an occlusion procedure. Other time-scale bands may also provide information indicative of blood pressure. For example, a secondary ridge associated with a scale higher than a pulse scale may arise due to the double-humped morphology of an oscillation signal and may also provide information indicative of blood pressure. Blood pressure may be correlated with any of the above selected features, other suitable features, or any combination thereof.

The selected features may be localized, repetitive, or continuous within one or more regions of the suitable domain space representation of signal 416. The selected features may not necessarily be localized in a band, but may potentially be present in any region within a signal representation. For example, the selected features may be localized, repetitive, or continuous in scale or time within a wavelet transform surface. A region of a particular size and shape may be used to analyze selected features in the domain space representation of signal 416. The region's size and shape may be selected based at least in part on the particular feature to be analyzed. As an illustrative example, in order to analyze a patient's pulse band for one or more selected features, the region may be selected to have an upper and lower scale value in the time-scale domain such that the region covers a portion of the band, the entire band, or the entire band plus additional portions of the time-scale domain. The region may also have a selected time window width.

The bounds of the region may be selected based at least in part on expected locations of the features. For example, the expected locations may be based at least in part on empirical data of a plurality of patients. The region may also be selected based at least in part on patient classification. For example, an adult's pulse band location generally differs from the location of a neonatal patient's pulse band. Thus, a region selected for an adult may be different than a region selected for a neonate.

In some embodiments, a region may be selected based at least in part on features within a scalogram. For example, the scalogram for a patient may be analyzed to determine the location of a pulse band and its corresponding ridge. A pulse band ridge may be located using standard ridge detection techniques. In an embodiment, locating a ridge may include identifying locations (a*, b*) in a scalogram which satisfy the relationship $$\frac{\partial}{\partial a}\left(\frac{|T(a,b)|^2}{a}\right)\bigg|_{a=a^*,b=b^*} = 0, \quad (11)$$

and locations in the vicinity of the ridge of Eq. 11. Such locations may be orthogonal to the ridge of Eq. 11, and may have lower values of the quantity |T (a, b)|²/a. In an embodiment, locating a ridge may include identifying locations (a*, b*) in a scalogram which satisfy the relationship $$\frac{\partial}{\partial a}(|T(a,b)|^2)\bigg|_{a=a^*,b=b^*} = 0, \quad (12)$$

and locations in the vicinity of the ridge of Eq. 12. Such locations may be orthogonal to the ridge of Eq. 12, and may have lower values of the quantity |T (a, b)|².

Ridges may also be detected using the techniques described in Watson et al., U.S. application Ser. No. 12/245,326, filed Oct. 3, 2008, entitled "SYSTEMS AND METHOD FOR RIDGE SELECTION IN SCALOGRAMS OF SIGNALS," which is incorporated by reference herein in its entirety. As an illustrative example, if the ridge of a band were found to be at location X, the region may be selected to extend a predetermined distance above and below location X. Alternatively, the band itself may be analyzed to determine its size. The upper and lower bounds of the band may be determined using one or more predetermined or adaptive threshold values. For example, the upper and lower bounds of the band may be determined to be the location where the band crosses below a threshold. The width of the region may be a predetermined amount of time or it may vary based at least in part on the characteristics of the original signal or the scalogram. For example, if noise is detected, the width of the region may be increased or portions of the region may be ignored.

In some embodiments, a region may be determined based at least in part on the repetitive nature of the selected features. For example, a band may have a periodic feature. The period of the feature may be used to determine bounds of the region in time and/or scale.

The size, shape, and location of one or more regions may also be adaptively manipulated using signal analysis. The adaptation may be based at least in part on changing characteristics of the signal or features within the various domain spaces.

As a signal is being processed, for example, by processor 412, the region may be moved over the signal in any suitable domain space over any suitable parameter in order to determine the value or change in value of the selected features. The processing may be performed in real-time or via a previously-recorded signal. For example, a region may move over the pulse band in the time-scale domain over time.

A physiological measurement, such as a blood pressure, may be provided to be displayed on a display (e.g., display 28). Blood pressure may be displayed textually or graphically on a display by depicting values or changes in values of the determined blood pressure or of the selected features described above. The graphical representation may be displayed in one, two, or more dimensions and may be fixed or change with time. The graphical representation may be further enhanced by changes in color, pattern, or any other visual representation.

The depiction of blood pressure measurements and changes in blood pressure measurements through a graphical, quantitative, qualitative representation, or combination of representations may be presented on output 414 and may be controlled by processor 412. In some embodiments, a display and/or speaker on output 414 may be configured to produce visual and audible alerts, respectively, when certain blood pressure conditions and changes in blood pressure are detected that may represent a patient's physiological state. Visual alerts may be displayed on, for example, display 28 and audible alerts may be produced on, for example, speaker 22. In some embodiments, processor 412 may determine whether or not to produce visual, audible, or a combination of alerts.

Figure 5:
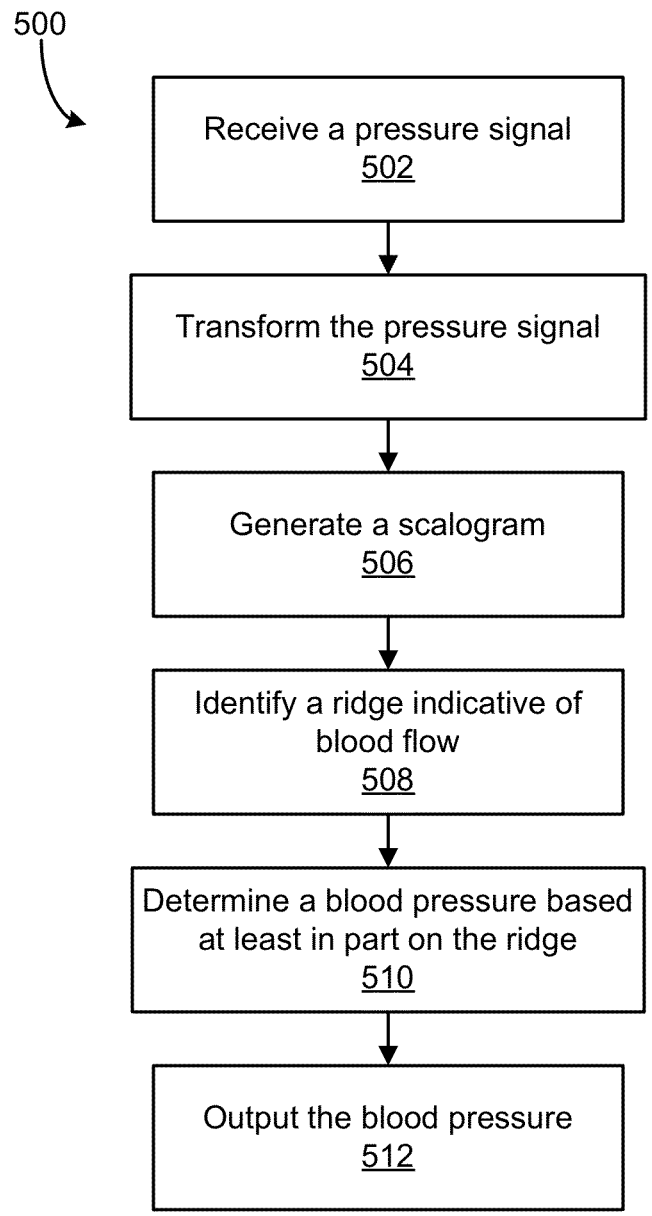
FIG. 5 is a flow diagram of illustrative steps involved in determining blood pressure from a pressure signal in accordance with an embodiment.
Figure 6A:
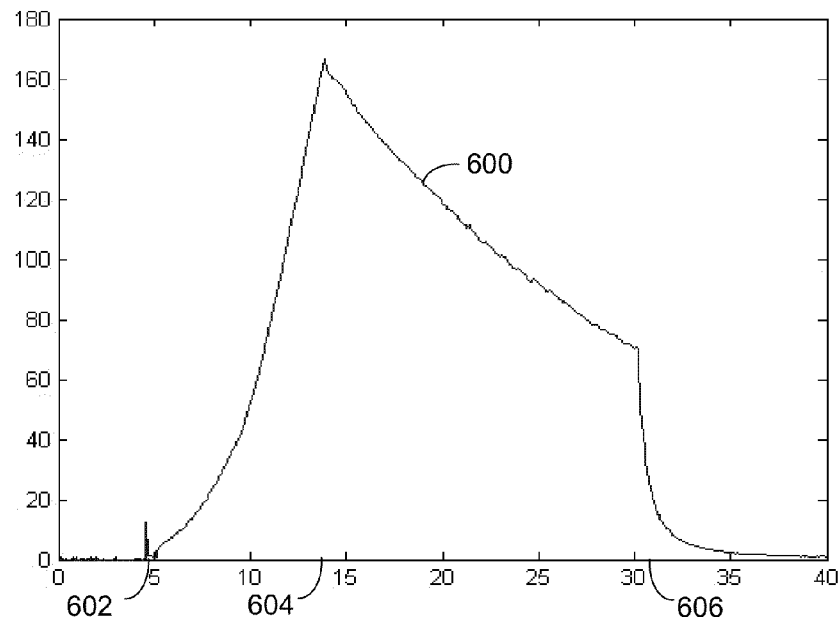
FIG. 6(a) depicts an illustrative pressure signal obtained during an occlusion procedure in accordance with an embodiment.
Figure 6B:
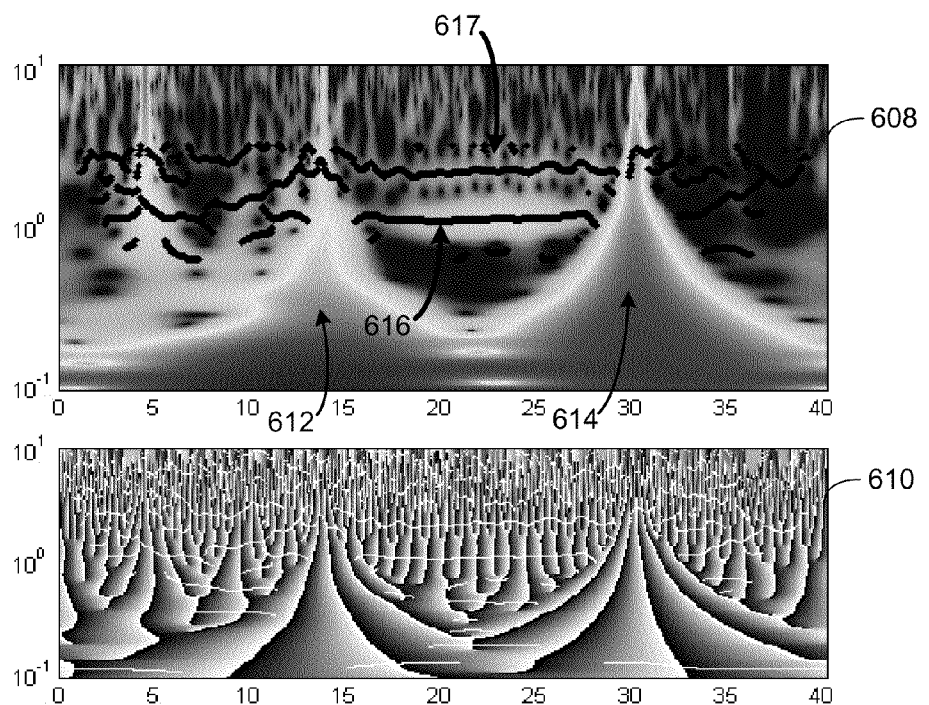
FIG. 6(b) depicts an illustrative scalogram of the pressure signal of FIG. 6(a) in accordance with an embodiment.
Figure 6C:
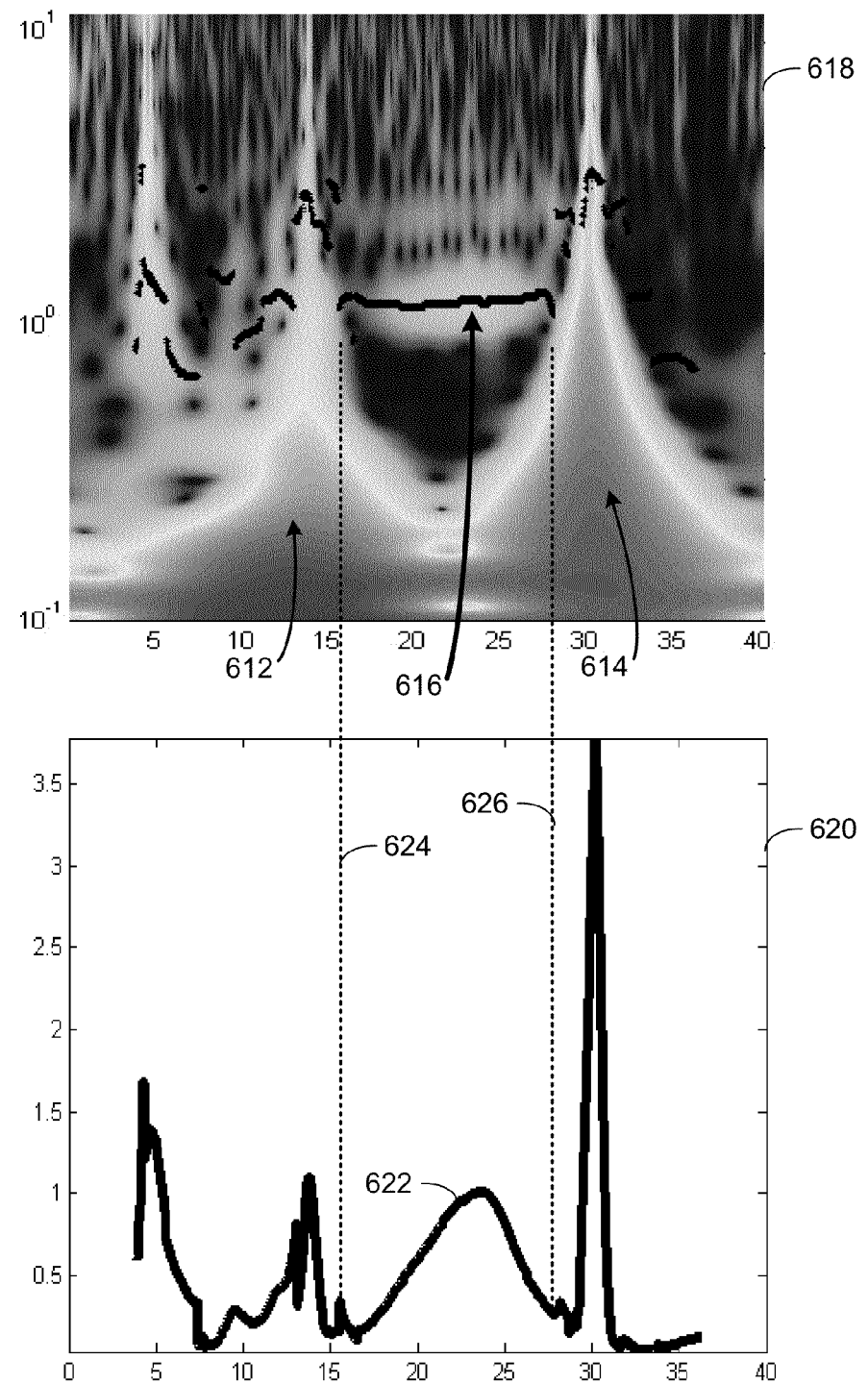
FIG. 6(c) shows an illustrative pulse ridge and corresponding oscillation envelope obtained from the scalogram of FIG. 6(b) in accordance with an embodiment.
Figure 6D:
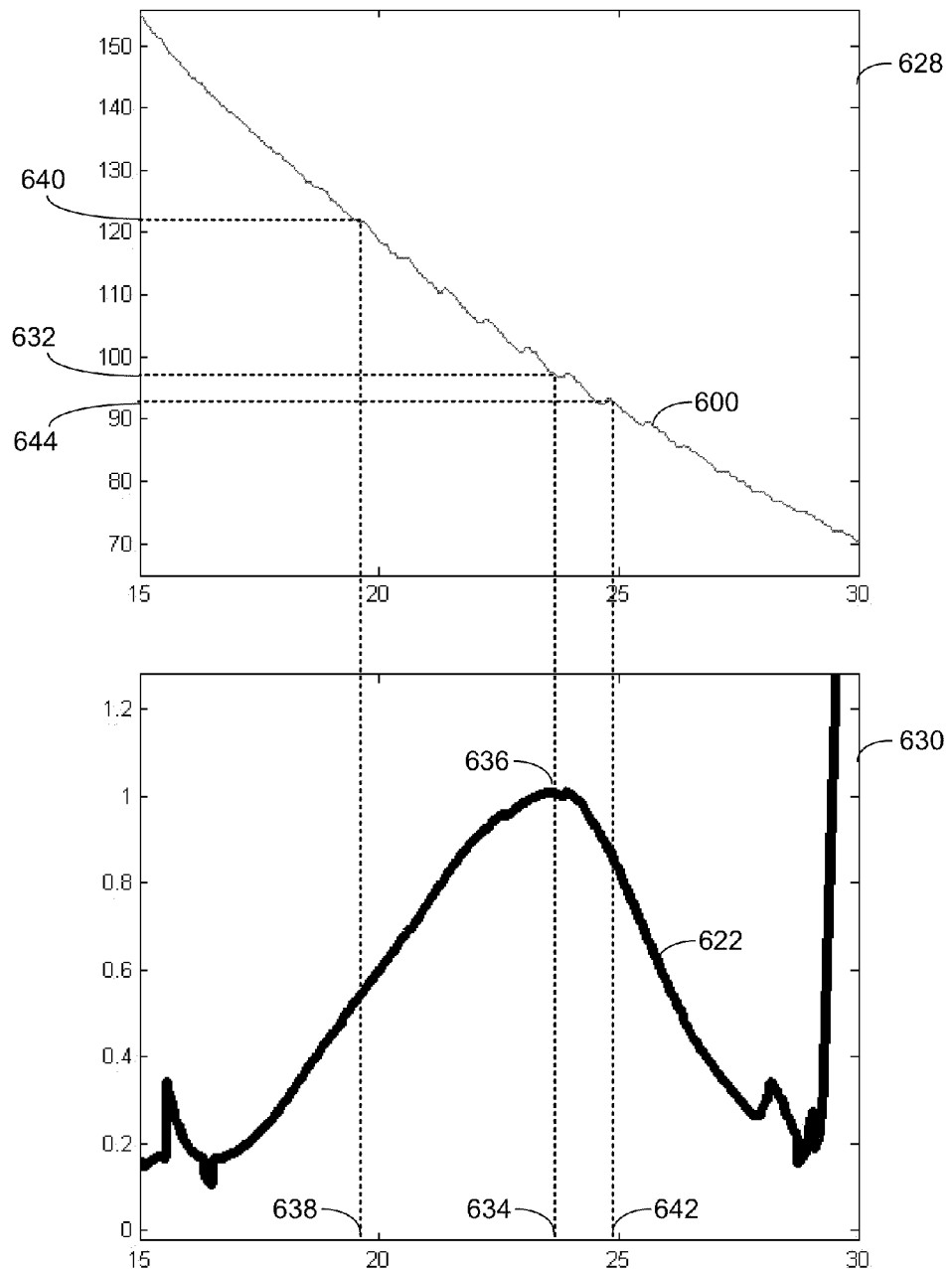
FIG. 6(d) illustrates a blood pressure determination technique applied to the pressure signal of FIG. 6(a) and the oscillation envelope of FIG. 6(c) in accordance with an embodiment.

FIG. 5 is a flow diagram 500 of illustrative steps involved in determining blood pressure from a pressure signal in accordance with an embodiment. The steps of flow diagram 500 may be performed by processor 412, or may be performed by any suitable processing device communicatively coupled to monitor 14. The steps of flow diagram 500 may be performed by a digital processing device, or implemented in analog hardware.

At step 502, a pressure signal is received. In an embodiment, a pressure signal may be an electronic signal representative of a physiological pressure signal, such as a signal representing a pulsatile force exerted by a patient's circulatory system. The signal may be received from any suitable source (e.g., patient 40) using any suitable technique. For example, the received signal may be generated at occluding device 12, which may itself include any of the physiological and/or pressure sensors described herein. In an embodiment, the signal received at step 502 may be an electronic signal responsive to an occluding device applied to a patient. As described above with reference to sensor 18, a pressure signal may be obtained by a pressure transducer, an optical sensor, or any sensor capable of detecting a physiological pressure or force. In an embodiment, the pressure signal is obtained as an occlusion procedure is performed on a patient. The pressure signal may be obtained by a sensor contained within an occluding device, such as sensor 18 of occluding device 12. In an embodiment, the pressure signal may be obtained by a sensor that is separate from an occluding device. In an embodiment, both the sensor and the occluding device may be in communication with monitor 14.

The received signal may be signal 416, which may be generated by a pre-processor 420 coupled between processor 412 and sensor 418. The received signal may include multiple signals, for example, in the form of a multi-dimensional vector signal or a frequency- or time-multiplexed signal. For example, multiple pressure signals may arise from multiple pressure sensors included in occluding device 12. In an embodiment, a pressure signal may be obtained from patient 40 using sensor 12 or input signal generator 410 in real time. In an embodiment, the pressure signal may have been stored in ROM 52, RAM 52, and/or QSM 72 in the past and may be accessed and/or processed by microprocessor 48 within monitor 14.

At step 504, the signal received at step 502 may be transformed. In an embodiment, processor 412 may transform the signal into any suitable domain such as, for example, any of a Fourier, wavelet, spectral, scale, time, time-spectral, time-scale domain, a domain based on any suitable basis function, any other transform space, or any combination thereof. The transformation may be performed by any one or more of the transformation techniques described herein, including a continuous wavelet transformation. This transformation may be performed by any suitable processing device, such as processor 412, which may itself be a general-purpose computing device or a specialized processor. The transformation may be performed by a separate, dedicated device. Processor 412 may further transform the original and/or transformed signals into any suitable domain. In an embodiment, step 504 is based at least in part on a continuous wavelet transformation. For example, a pressure signal may be transformed using a continuous wavelet transform as described above with reference to FIGS. 3(*a*)-3(*f*).

Any number of computational and/or optimization techniques may be performed in conjunction with the transformation of step 504. For example, if one or more scale bands associated with circulatory processes are approximately known or may be detected, the transformation may initially be executed only over scales in or close to these scale bands in order to reduce computation time. For example, if a patient's pulse rate is approximately known, the transformation may initially be executed only over scales at or close to the scale bands associated with the pulse rate (i.e., the pulse band). In an embodiment, if one or more scale bands communicate questionable or little information about a physiological process of interest, a transformation may not be executed over these scale bands. Any known information about any scale bands of interest may be stored in memory (e.g., ROM 52 or RAM 54). Such known information may be keyed to the characteristics of the patient, which may be input via user inputs 56 and used by monitor 14 to, for example, query a lookup table and retrieve the appropriate information. Additionally, any of the calculations and computations described herein may be optimized for a particular hardware implementation, which may involve implementing any one or more of a pipelining protocol, a distributed computational technique, a memory management technique, or any suitable optimization technique.

The transformation of the received signal at step 504 may also include pre- or post-processing transformations. These transformation may include any one or more of the following: compressing, multiplexing, modulating, up-sampling, down-sampling, smoothing, taking a median or other statistic of the received signal, removing a mean value or windowed mean value of the received signal, removing erroneous regions of the received signal, or any combination thereof.

In an embodiment, at step 504, the signal may be filtered using any suitable filtering method. In an embodiment, a signal received at sensor 12 may be filtered by filter 68 prior to undergoing additional processing at microprocessor 48 within patient monitoring system 10. The filter 68 may selectively remove frequencies that may be ignored by the transformation, which may advantageously reduce computational time and memory requirements. In an embodiment, the signal received at step 502 may be high or band pass filtered to remove frequencies. For example, a pressure signal may be filtered through a narrow band-pass filter that may be centered on the scale of a ridge of a scale band of interest, such as the pulse band. The received signal may be filtered through any suitable additional number and type of filters that may be centered on the scales of different ridges of interest. In an embodiment, the filter 68 is a band-pass filter which may allow frequencies in the approximate range 0-30 Hz. In an embodiment, the cutoff frequencies of a filter are chosen based on the frequency response of the hardware platform underlying blood pressure monitoring system 10.

Different transformations may be applied to a portion or portions of the received signal. In an embodiment, a portion of the pressure signal may include an oscillation signal that may be used to determine blood pressure (e.g., portion 108 of pressure signal 100 of FIG. 1). A transformation may be applied only to this portion of the pressure signal. The transformation of step 504 may be broken into one or more stages performed by one or more devices within wavelet processing system 400 (which may be a part of blood pressure monitoring system 10). For example, a filtering operation may be applied by input signal generator 410 prior to passing the resulting input signal 416 to processor 412, where it may undergo additional transformations. Embodiments of step 504 include any of the transformations described herein performed in any suitable order.

At step 506, a scalogram may be generated based at least in part on the transformed signal of step 504. Examples of scalograms are depicted in FIGS. 3(*a*), 3(*b*), 6(*b*) and 6(*c*). A scalogram may be generated by any of the techniques described herein, including those described above with reference to FIGS. 3(*a*) and 3(*b*). For example, processor 412 or microprocessor 48 may perform the calculations associated with the continuous wavelet transform of a signal and the derivation of the scalogram. As described above with reference to step 504, if one or more scale bands associated with blood flow processes are approximately known or may be detected, the scalogram may be generated only over scales at or close to these scale bands in order to reduce computation time. In an embodiment, if one or more scale bands communicate questionable or little information about blood flow, the scalogram may not be generated over these scale bands. In an embodiment, the scalogram generated at step 506 may be displayed for a user in any manner described herein, including via displays 20 and/or 28. The scalogram may also be recorded to a memory device (e.g., RAM 54 or a remote storage device) or a physical medium such as a print-out. In an embodiment, the scalogram generated at step 506 is based at least in part on any one or more features of the transformed signal of step 504. For example, the scalogram may represent the real part of a transformed signal, the imaginary part of a transformed signal, the modulus of a transformed signal, any other suitable feature of a transformed signal, or any combination thereof.

Once a scalogram has been generated at step 506, a ridge may be identified within the scalogram at step 508. An identified ridge may be indicative of blood flow, and may contain information that may be used to determine blood pressure. In an embodiment, an identified ridge may be a ridge of a pulse band of the scalogram generated at step 506. A ridge may be identified using any of the techniques described above, including identifying local maxima of a scalogram. In an embodiment, more than one ridge identification technique may be used at step 508. In an embodiment, more than one ridge may be identified, each of which may communicate additional information about a patient's blood flow. For example, a primary ridge and a secondary ridge may be identified at step 508, and information from both may be used to determine blood pressure. In an embodiment, multiple ridges may be detected in a scalogram at step 508, but only a subset of the identified ridges may be used for blood pressure determination.

In an embodiment, other features of a scalogram may be identified at step 508 in addition to a ridge. For example, sudden changes in the pressure applied to a patient by an occluding device, such as occluding device 12, may correspond to scale edge features in the scalogram of a pressure signal derived from the patient, as discussed in additional detail below with reference to FIG. 6(*b*). These scale edge features may be used to identify the period during which blood flow was impeded by an occluding device, the nature and intensity of the occlusion, or additional phenomena.

The scalogram ridge identified at step 508 may be used to determine a blood pressure at step 510. In an embodiment, a suitable projection of the scalogram ridge may be performed at step 510. For example, the ridge may be projected onto a time-scale plane, a time-phase plane, a time-modulus plane or a time-amplitude plane. In an embodiment, a projection of the ridge identified at step 508 onto a time-amplitude plane or time-modulus plane may provide an oscillation envelope that may be used to determine blood pressure. This oscillation envelope may describe the amplitude of an oscillation signal component of a pressure signal obtained during an occlusion procedure, as described above. For example, step 510 may include the calculation of oscillation envelope 126 of oscillation signal 110 of FIG. 1. An oscillation envelope may be used to determine blood pressure in accordance with the oscillometric techniques described above with reference to FIG. 1. The blood pressure measurement generated at step 510 may include one or more blood pressure measurements, such as systolic blood pressure, diastolic blood pressure, mean arterial pressure, or any other characterization of the pressures exerted by a patient's circulatory system. Additional embodiments of methods for determining blood pressure using an oscillation envelope as provided by process 500 are discussed in detail below with reference to FIGS. 6(*a*)-6(*d*).

At step 512, the blood pressure measurement determined at step 510 may be output. A blood pressure measurement may be output through a graphical representation, quantitative representation, qualitative representation, or combination of representations via output 414 and may be controlled by processor 412. Output 414 may transmit a blood pressure measurement by any means and through any format useful for informing a patient and a care provider of a patient status and/or recording physiological information to a storage medium. For example, a patient's blood pressure may be communicated numerically (e.g., as systolic and diastolic measurements or a ratio of the two measurements). A patient's blood pressure may be communicated qualitatively, such as a designation of "high blood pressure," "low blood pressure" or "normal blood pressure." Qualitative assessments of blood pressure may be based on any combination of patient information (e.g., demographic information), physiological status (e.g., following a severe trauma), or therapeutic intervention (e.g., after the administration of a vasodilator). The quantitative or qualitative blood pressure information may be provided by output 414 to be displayed on a display (e.g., display 28). The graphical representation may be displayed in one, two, or more dimensions and may be fixed or change with time. The graphical representation may be further enhanced by changes in color, pattern, or any other visual representation. Output 414 may communicate the blood pressure information by performing at least one of the following: presenting a screen on a display; presenting a message on a display; producing a tone or sound; changing a color of a display or a light source; producing a vibration; and sending an electronic message. Output 414 may perform any of these actions in a device close to the patient, or at a mobile or remote monitoring device as described previously. In an embodiment, output 414 produces a continuous tone or beeping whose frequency changes in response to changes in a measured blood pressure. In an embodiment, output 414 produces a colored or flashing light which changes in response to changes in a measured blood pressure.

After or during the output of physiological information at step 512, the steps of flow diagram 500 may begin again. Either a new signal may be received, or the blood pressure determination may continue on another portion of the received signal(s). In an embodiment, processor 412 may continuously or periodically perform steps 502-512 and update the blood pressure measurement. The process may repeat indefinitely, until there is a command to stop the monitoring and/or until some detected event occurs that is designated to halt the monitoring process. For example, it may be desirable to halt a monitoring process when a detected noise has become too great, or when a patient has undergone a change in condition that can no longer be sufficiently well-monitored in a current configuration. In an embodiment, processor 412 performs the steps of flow diagram 500 at a prompt from a care provider via user inputs 56. In an embodiment, processor 412 performs the steps of flow diagram 500 at intervals that change according to patient status. For example, the steps of flow diagram 500 may be performed more often when a patient is undergoing rapid changes in physiological condition, and may be performed less often as the patient's condition stabilizes. Additional illustrative embodiments of blood pressure determination systems and techniques will now be discussed with reference to FIGS. 6(*a*)-6(*d*).

FIG. 6(*a*) depicts an illustrative pressure signal 600 that may be obtained during an occlusion procedure. Pressure signal 600 may be the signal received at step 502 of flow diagram 500, or may be a filtered version of such a received signal. Pressure signal 600 may arise as described above with reference to pressure signal 100 of FIG. 1. For example, pressure signal 600 may be measured at a patient during the following occlusion procedure:

1. At time point 602 (which occurs approximately five seconds into the measurement), the pressure applied to the patient by a occluding device begins to increase.

2. The applied pressure reach a peak at time point 604 (which occurs approximately 14 seconds into the measurement).
3. The applied pressure gradually decreases.
4. The applied pressure is released at time point 606 (which occurs approximately 30 seconds into the measurement).

FIG. 6(*b*) is a representation of a scalogram derived from a continuous wavelet transformation of pressure signal 600. The scalogram represented in FIG. 6(*b*) may be generated at step 506 of flow diagram 500 after a continuous wavelet transformation performed at step 504. Plot 608 may represent the modulus of a complex-valued scalogram, while plot 610 may represent the phase of the complex-valued scalogram. Plots 608 and 610 may include large scale edge features corresponding to the point of maximum pressure (i.e., time 604) and the point of pressure release (i.e., time 606). For example, dominant "wedge" 612 may correspond to the point of maximum pressure applied by the occluding device, while "wedge" 614 may correspond to the point at which the occluding device releases pressure. In an embodiment, scale edge features may be used to indicate significant points in the occlusion procedure as applied to a patient.

Plot 608 also includes an indication of the location of a ridge 616. Ridge 616 may be identified at step 508 of flow diagram 500, for example, using any of the ridge identification/detection techniques disclosed herein. Ridge 616 may be a pulse band ridge, and may be located between the scale edge features 612 and 614. Ridge 616 may be considered a primary ridge because of its dominance within the pulse band of the scalogram. A secondary ridge 617 is also indicated in plot 608. Ridge 617 may be located at a higher scale than ridge 616. A secondary ridge such as ridge 617 may arise because of pressure signal characteristics (e.g., the double-humped morphology of an oscillometric signal), artifacts in the pressure signal (e.g., those caused by patient movement), noise (e.g., interference or disruption affecting sensor 18 of occluding device 12), or any combination thereof. In an embodiment, one or more ridges may be identified in a scalogram. These ridges may be used to determine blood pressure as described above with reference to step 510 of flow diagram 500; additional embodiments are described in detail below.

At the top of FIG. 6(*c*), plot 618 represents the modulus of the scalogram of pressure signal 600 and is a resized version of plot 608. As described with reference to plot 608, plot 618 includes an indication of ridge 616 between the two scale edge features 612 and 614. At the bottom of FIG. 6(*c*), plot 620 depicts oscillation envelope 622 based at least in part on ridge 616. Dotted lines 624 and 626 indicate corresponding time points in the scalogram of plot 618 and oscillation envelope 622 of plot 620. In an embodiment, oscillation envelope 622 may be a projection of ridge 616 onto the time-modulus plane. In an embodiment, oscillation envelope 622 may be the projection of ridge 616 onto a time-amplitude plane. In an embodiment, oscillation envelope 622 may be the projection of ridge 616 onto another suitable plane in wavelet space, which may or may not be orthogonal to the time-modulus plane. In an embodiment, a projection may be performed after generating a scalogram of a pressure signal, such as a scalogram generated by a continuous wavelet transformation, by removing the scale component of three-dimensional ridge 616. In an embodiment, a projection may be performed by using standard linear algebraic projection techniques applied to one or more ridges identified in a scalogram. In an embodiment, a projection may be a non-linear projection, such as a spherical or hyperbolic projection, onto a suitable surface or subspace. A projection of the identified ridge to obtain an oscillation envelope may advantageously allow the determination of blood flow and blood pressure information from the pressure signal, while eliminating the influence of spurious or noisy regions of a scalogram. Such a method may also reduce the time required for the occlusion procedure and improve blood pressure measurement resolution and accuracy.

In an embodiment, one or more portions of ridge 616 may be used in a blood pressure determination procedure. For example, an occlusion procedure may include one or more periods of pressure applied to a patient between release. Each of these periods may be represented in different portions of ridge 616, and may therefore contribute to an oscillation envelope or envelopes in varying ways. Embodiments that combine the blood pressure information obtained during such multiple occlusion procedures are within the scope of this disclosure. In an embodiment, an oscillation envelope may be obtained by combining several oscillation envelopes from one or more occlusion procedures. For example, multiple oscillation envelopes may be averaged, used to find a median envelope, or combined in any suitable manner.

FIG. 6(*d*) illustrates a blood pressure determination technique applied to pressure signal 600 of FIG. 6(*a*) and oscillation envelope 622 of FIG. 6(*c*). Plot 628 depicts a portion of pressure signal 600 between time points 604 and 606 (i.e., during the gradual decrease in pressure applied by the occluding device). Plot 630 depicts a portion of oscillation envelope 622 between the same time points.

In an embodiment, the value of pressure signal 600 at the time corresponding to the peak amplitude of oscillation signal 622 may provide a measurement of the mean arterial pressure. For example, mean arterial pressure 632 may be measured by identifying time point 634 corresponding to the peak amplitude 636 of oscillation signal 622, and determining the value 632 of pressure signal 600 at time point 634.

In an embodiment, at least one of a systolic and a diastolic blood pressure may be determined from oscillation signal 622. In an embodiment, the value of pressure signal 600 at a time corresponding to a particular amplitude of oscillation signal 622 may provide a measurement of the systolic blood pressure. This particular amplitude may be related to the peak amplitude by a scale factor (e.g., a multiplicative factor in the range 0.5-0.55). For example, FIG. 6(*d*) illustrates time point 638, at which the amplitude of oscillation signal 622 may be approximately equal to the peak amplitude multiplied by a scale factor of 0.55. A patient's systolic blood pressure may be measured by identifying the value 640 of pressure signal 600 at time point 638.

In an embodiment, the value of pressure signal 600 at a time corresponding to a particular amplitude of oscillation signal 622 may provide a measurement of the diastolic blood pressure. This particular amplitude may be related to the peak amplitude by a scale factor (e.g., a multiplicative factor in the range 0.7-0.85). For example, FIG. 6(*d*) illustrates time point 642, at which the amplitude of oscillation signal 622 may be approximately equal to the peak amplitude multiplied by a scale factor of 0.85. A patient's diastolic blood pressure may be measured by identifying the value 644 of pressure signal 600 at time point 642.

Figure 7:
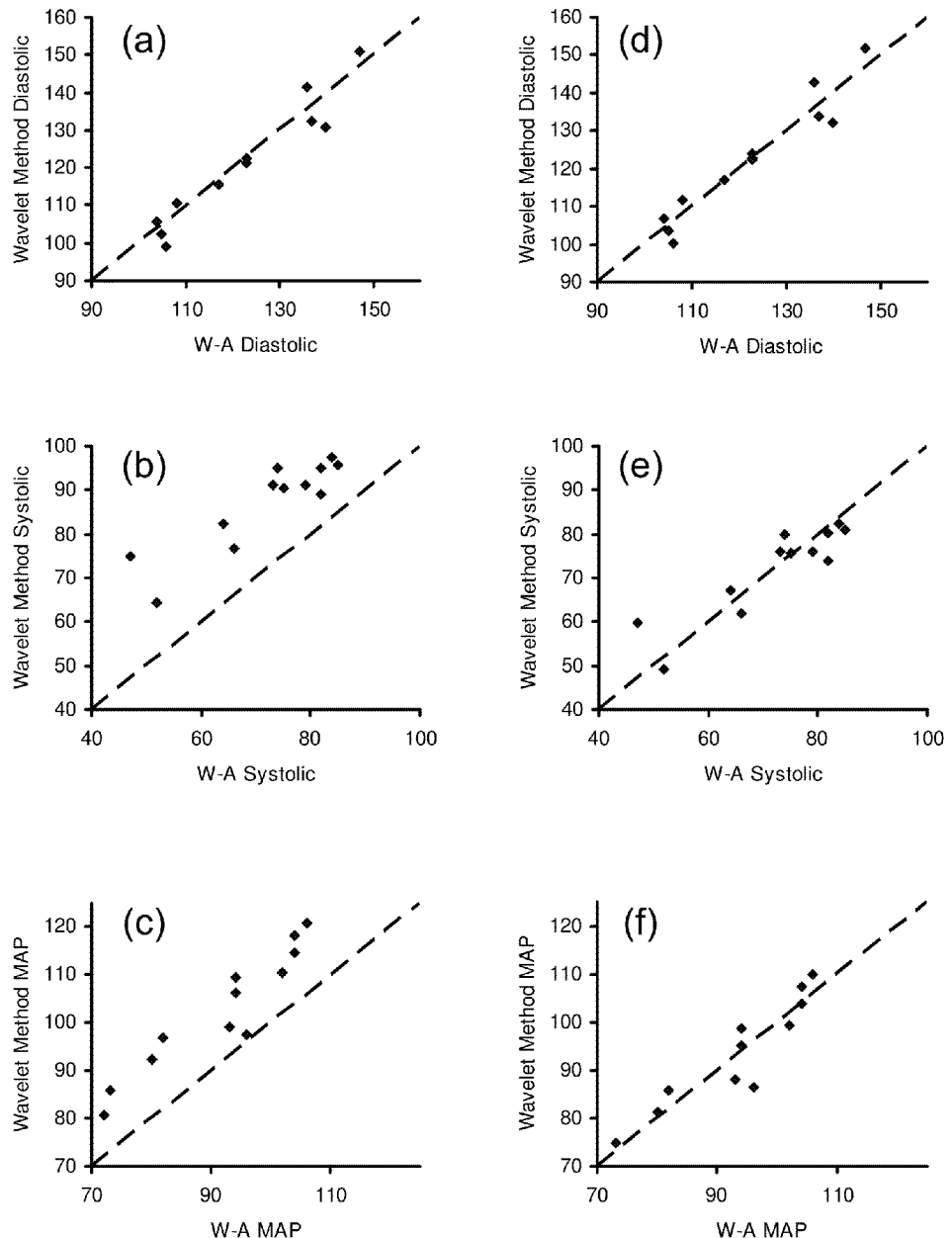
FIGS. 7(a)-7(f) depict blood pressure data obtained using the illustrative steps of the flow diagram of FIG. 5 in accordance with an embodiment.

FIGS. 7(*a*)-7(*c*) depict blood pressure data obtained by applying an embodiment of the steps of flow diagram 500 as illustrated in FIG. 5. Twelve blood pressure signals (as described above with reference to pressure signal 100 and pressure signal 600) were obtained from patient volunteers. These signals were detected by a Welsh-Allyn (W-A) Propaq machine. The signals were obtained from the W-A machine and analyzed using a continuous wavelet transform embodiment of the method of process 500 of FIG. 5. Additionally, the W-A machine was programmed with its own blood pressure determination routine, the results of which were compared against the results obtained using a continuous wavelet transform technique as disclosed herein. FIGS. 7(a)-7(c) each plot the 12 blood pressure values determined by a continuous wavelet transform embodiment of the steps of flow diagram 500 against the values produced by the W-A machine routine (labeled "W-A"). The diagonal dashed lines in each of FIGS. 7(a)-7(c) indicate the points along which the W-A and continuous wavelet transform methods agree. FIGS. 7(a)-7(c) exhibit a fairly constant offset between the W-A measurements and the continuous wavelet transform technique results for each of mean arterial pressure, systolic pressure and diastolic pressure.

FIGS. 7(d)-7(f) depict the same blood pressure data as depicted in FIGS. 7(a)-7(c), but with the mean deviation between the W-A and continuous wavelet transform technique removed from each of the three measurement data sets. FIGS. 7(d)-7(f) illustrate a strong agreement between the measurements obtained by the W-A machine and the measurements obtained from the continuous wavelet transform embodiment of process 500. These results indicate that the blood pressure determination techniques described herein yield comparable results to existing commercial devices, while providing the additional computational and performance advantages noted above.

It will be understood that the above method may be implemented using any human-readable or machine-readable instructions on any suitable system or apparatus, such as those described herein.

The foregoing is merely illustrative of the principles of this disclosure and various modifications can be made by those skilled in the art without departing from the scope and spirit of the disclosure. The following claims may also describe various aspects of this disclosure.

What is claimed is:

1. A method for determining a blood pressure measurement, comprising:
    receiving, from a sensor, an electronic signal responsive to an occluding device applied to a patient;
    using processor equipment for:
        transforming the electronic signal into a transformed signal based at least in part on a continuous wavelet transformation,
        generating a scalogram based at least in part on the transformed signal, wherein the scalogram comprises 3-dimensional information,
        identifying, within the scalogram, a ridge indicative of the patient's blood flow as a function of time, and
        determining a blood pressure measurement based at least in part on the identified ridge; and
    outputting the blood pressure measurement to an output device.

2. The method of claim 1, further comprising applying a variable occluding pressure to a patient using the occluding device.

3. The method of claim 1, wherein the sensor is a pressure transducer associated with the occluding device.

4. The method of claim 1, wherein the blood pressure measurement comprises at least one of a systolic blood pressure, a diastolic blood pressure and a mean arterial pressure.

5. The method of claim 1, further comprising using processor equipment for determining an oscillation envelope based at least in part on the identified ridge, wherein determining a blood pressure measurement is based at least in part on the oscillation envelope.

6. The method of claim 5, wherein the oscillation envelope is based at least in part on a projection of the identified ridge.

7. The method of claim 1, wherein determining a blood pressure measurement is further based at least in part on a maximum amplitude of the identified ridge.

8. A system for determining a blood pressure measurement, comprising:
    an occluding device capable of being applied to a patient;
    a sensor, coupled to the occluding device, that outputs an electronic signal responsive to the occluding device when the occluding device is applied to the patient;
    processor equipment, coupled to the sensor, the processor equipment being capable of:
        transforming the electronic signal into a transformed signal based at least in part on a continuous wavelet transformation,
        generating a scalogram based at least in part on the transformed signal, wherein the scalogram comprises 3-dimensional information,
        identifying, within the scalogram, a ridge indicative of the patient's blood flow as a function of time,
        determining a blood pressure measurement based at least in part on the identified ridge; and
    an output device, coupled to the processor equipment, for outputting the blood pressure measurement.

9. The system of claim 8, wherein the occluding device is capable of applying a variable occluding pressure to a patient.

10. The system of claim 8, wherein the sensor is a pressure transducer associated with the occluding device.

11. The system of claim 8, wherein the blood pressure measurement comprises at least one of a systolic blood pressure, a diastolic blood pressure and a mean arterial pressure.

12. The system of claim 8, wherein the processor equipment is further capable of determining an oscillation envelope based at least in part on the identified ridge, wherein determining a blood pressure measurement is based at least in part on the oscillation envelope.

13. The system of claim 12, wherein the oscillation envelope is based at least in part on a projection of the identified ridge.

14. The system of claim 8, wherein determining a blood pressure measurement is further based at least in part on a maximum amplitude of the identified ridge.

15. Non-transitory computer-readable medium for use in determining a blood pressure measurement, the computer-readable medium having computer program instructions recorded thereon for:
    receiving, from a sensor, an electronic signal responsive to an occluding device applied to a patient,
    transforming the electronic signal into a transformed signal based at least in part on a continuous wavelet transformation,
    generating a scalogram based at least in part on the transformed signal, wherein the scalogram comprises 3-dimensional information,
    identifying, within the scalogram, a ridge indicative of the patient's blood flow as a function of time,
    determining a blood pressure measurement based at least in part on the identified ridge, and
    outputting the blood pressure measurement to an output device.

16. The non-transitory computer-readable medium of claim 15, further having computer program instructions recorded thereon for directing the occluding device to apply a variable occluding pressure to a patient.

17. The non-transitory computer-readable medium of claim 15, wherein the sensor is a pressure transducer associated with the occluding device.

18. The non-transitory computer-readable medium of claim 15, wherein the blood pressure measurement comprises at least one of a systolic blood pressure, a diastolic blood pressure and a mean arterial pressure.

19. The non-transitory computer-readable medium of claim 15, further having computer program instructions recorded thereon for determining an oscillation envelope based at least in part on the identified ridge, wherein determining a blood pressure measurement is based at least in part on the oscillation envelope.

20. The non-transitory computer-readable medium of claim 19, wherein the oscillation envelope is based at least in part on a projection of the identified ridge.

* * * * *